(12) United States Patent
Smart et al.

(10) Patent No.: US 9,052,261 B2
(45) Date of Patent: Jun. 9, 2015

(54) DYNAMIC AND DEPOLARIZED DYNAMIC LIGHT SCATTERING COLLOID ANALYZER

(71) Applicant: Scattering Solutions, Inc., Irvine, CA (US)

(72) Inventors: Anthony E. Smart, Costa Mesa, CA (US); William V. Meyer, Lakewood, OH (US); Craig J. Saltiel, Irvine, CA (US)

(73) Assignee: Scattering Solutions, Inc., Irvine, CA (US)

( * ) Notice: Subject to any disclaimer, the term of this patent is extended or adjusted under 35 U.S.C. 154(b) by 0 days.

(21) Appl. No.: 14/222,774

(22) Filed: Mar. 24, 2014

(65) Prior Publication Data

US 2014/0285800 A1 Sep. 25, 2014

Related U.S. Application Data

(63) Continuation of application No. 12/861,079, filed on Aug. 23, 2010, now Pat. No. 8,717,562.

(51) Int. Cl.
*G01N 15/02* (2006.01)
*G01N 15/10* (2006.01)
(Continued)

(52) U.S. Cl.
CPC ............ *G01N 15/10* (2013.01); *G01N 15/0211* (2013.01); *G01N 21/49* (2013.01); *G01N 21/51* (2013.01); *G01N 2015/0222* (2013.01);
(Continued)

(58) Field of Classification Search
CPC .......... G01N 15/0205; G01N 15/0211; G01N 15/1459; G01N 2021/4716; G01N 15/1434
USPC ........................................................ 356/336
See application file for complete search history.

(56) References Cited

U.S. PATENT DOCUMENTS

| | | |
|---|---|---|
| 4,975,237 A | 12/1990 | Watling |
| 5,946,092 A | 8/1999 | DeFreez et al. |
| 5,956,139 A | 9/1999 | Meyer et al. |

(Continued)

OTHER PUBLICATIONS

Auweter et al., "Fiber-optical quasi-elastic light scattering of concentrated dispersions" J. Colloid and Interface Sci., Jun. 1985 (date unknown), vol. 105, No. 2, pp. 399-409.

(Continued)

*Primary Examiner* — Tarifur Chowdhury
*Assistant Examiner* — Md Rahman
(74) *Attorney, Agent, or Firm* — Wolf, Greenfield & Sacks, P.C.

(57) ABSTRACT

Apparatus are described for measuring the characteristics of colloidal particles suspended in transparent media by Dynamic Light Scattering (DLS) and Depolarized Dynamic Light Scattering (DDLS) into regions where conventional measurements are difficult or impractical. Matching the diameter of an illuminating beam and an intersecting diameter of a field stop image extends measurements into regions that include concentrated turbid suspensions that frequently appear so visually opaque that multiple scattering typically gives a falsely low estimate of particle size. At the opposite extreme, where insufficient signal is available to determine either or both of the translational and/or rotational relaxation times of the particles, typically where they are too small, too few, or of insufficient refractive index difference from the medium to scatter enough light, measurements can be improved by: a) using a sufficiently large aperture such that many coherence areas fall upon the detector; and b) optical homodyne amplification of the scattered signal.

14 Claims, 14 Drawing Sheets

Homodyne Layout for Depolarization Measurements

(51) Int. Cl.
   *G01N 21/49* (2006.01)
   *G01N 21/51* (2006.01)
(52) U.S. Cl.
   CPC  *G01N2015/1087* (2013.01); *G01N 2015/1093* (2013.01)

(56) References Cited

U.S. PATENT DOCUMENTS

| | | | |
|---|---|---|---|
| 5,973,779 | A | 10/1999 | Ansari et al. |
| 6,016,195 | A | 1/2000 | Peters |
| 6,469,787 | B1 | 10/2002 | Meyer et al. |
| 2008/0221814 | A1 | 9/2008 | Trainer |
| 2012/0044493 | A1 | 2/2012 | Smart et al. |

OTHER PUBLICATIONS

Chayen et al., "Size and shape of proteins in solutions by a noninvasive depolarized dynamic light scattering instrument," Ann N Y Acad. Sci., Nov. 2004 (date unknown), vol. 1027, p. 20.

Chu, B., "Laser light scattering: Basic principles and practice," $2^{nd}$ Edition, Academic Press, 1991 (date and month unknown).

Degiorgio et al, "Forward depolarized light scattering: heterdyne versus homodyne detection" Physica A, Jan. 15, 1997, vol. 235, No. 1-2, pp. 279-290.

Office Action from U.S. Appl. No. 12/861,079 dated Nov. 18, 2013.

Lomakin et al., "Quasielastic light scattering for protein assembly studies," Methods in molecular biology, v. 299, Amyloid proteins: Methods and protocols, ed. Sigurdsson, Humana Press, 2005 (date and month unknown).

Office Action from U.S. Appl. No. 12/861,079 dated Apr. 4, 2013.

Notice of Allowance from U.S. Appl. No. 12/861,079 dated Dec. 24, 2013.

Phillies, G.D.J., "Experimental demonstration of multiple-scattering suppression in quasielastic-light-scattering spectroscopy by homodyne coincidence techniques," Phys. Rev. A , Oct. 1, 1981, vol. 24, p. 1939.

Phillies, G.D.J., "Suppression of multiple-scattering effects in quasielastic-light-scattering spectroscopy by homodyne cross-correlation techniques," J. Chem. Phys., Jan. 1, 1981, vol. 74, No. 1, pp. 260-262.

Pine et al., "Diffusing wave spectroscopy," Phys. Rev. Lett., Mar. 21, 1988, vol. 60, p. 1134.

Pusey et al., "Dielectric and related molecular processes" vol. 2, Ed. Mansel Davies, specialist periodical report, London: The Chemical Society, 1975 (date and month unknown).

Trainer et al., "High-concentration submicron particle size distribution by dynamic light scattering," American Laboratory, Jul. 1992 (date unknown).

Xu, R., "Particle characterization: Light scattering methods," Kluwer, 2000 (month and date unknown).

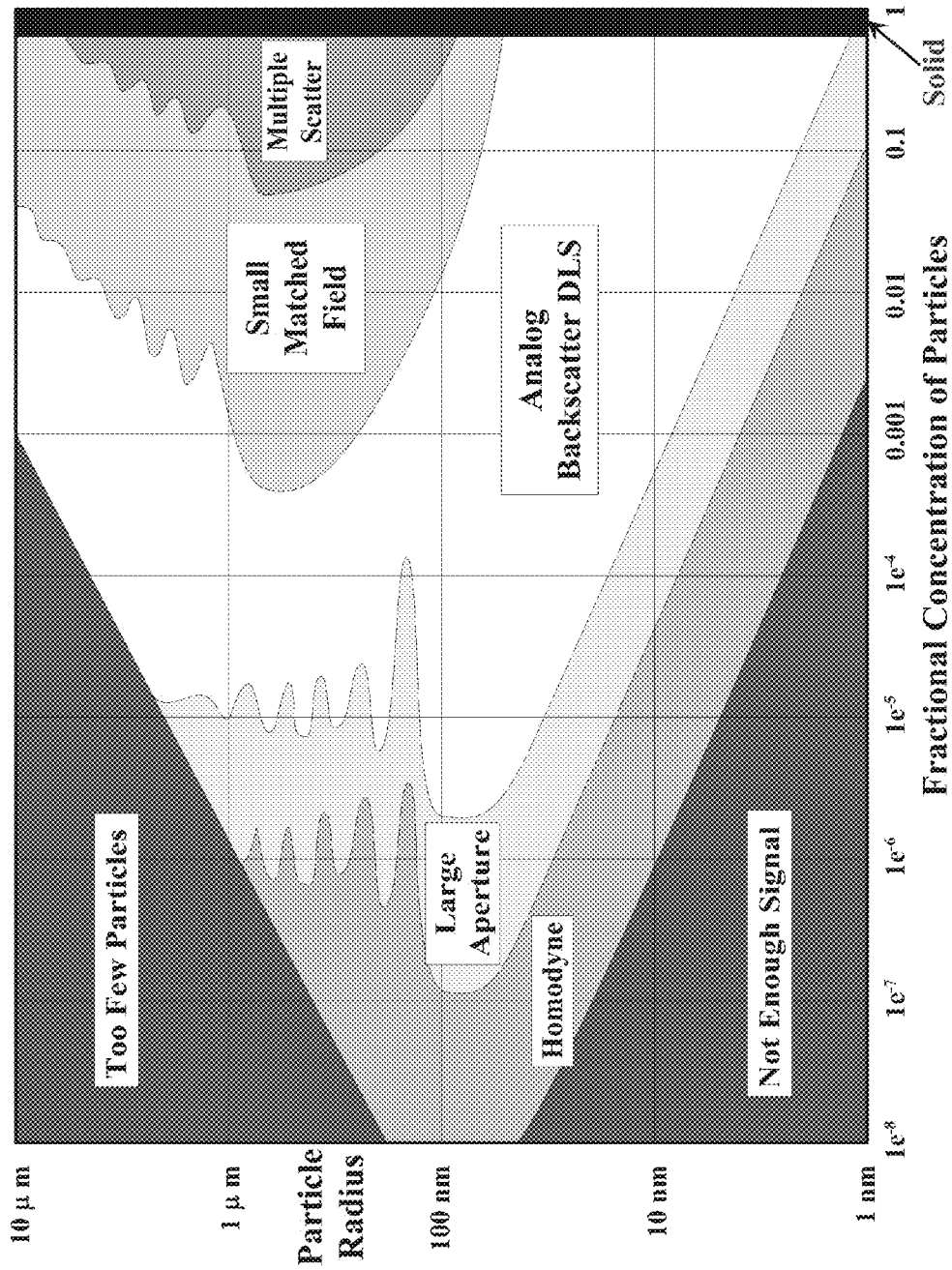
Figure 1  Extension of Boundaries of Applicability of DLS/DDLS

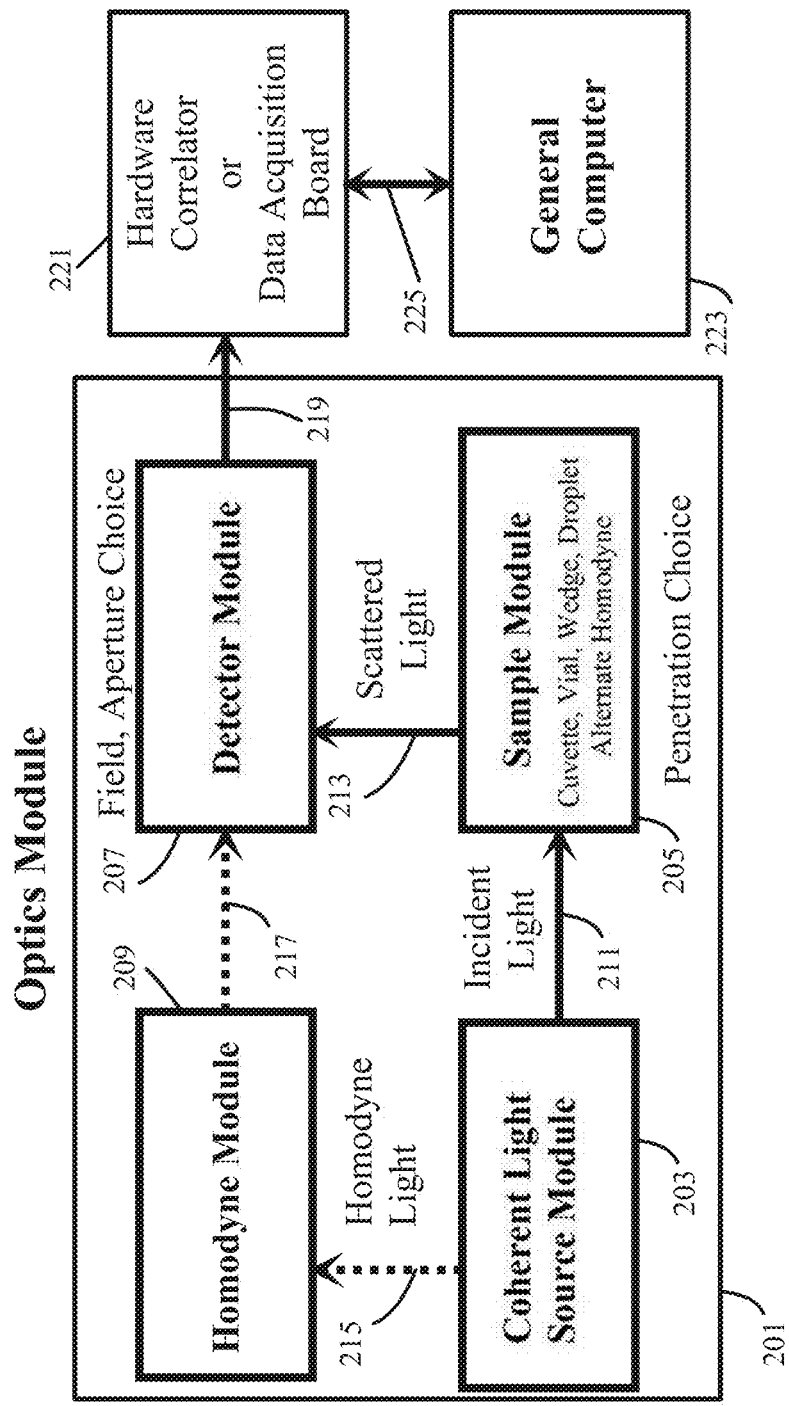
Figure 2 Colloid Analyzer

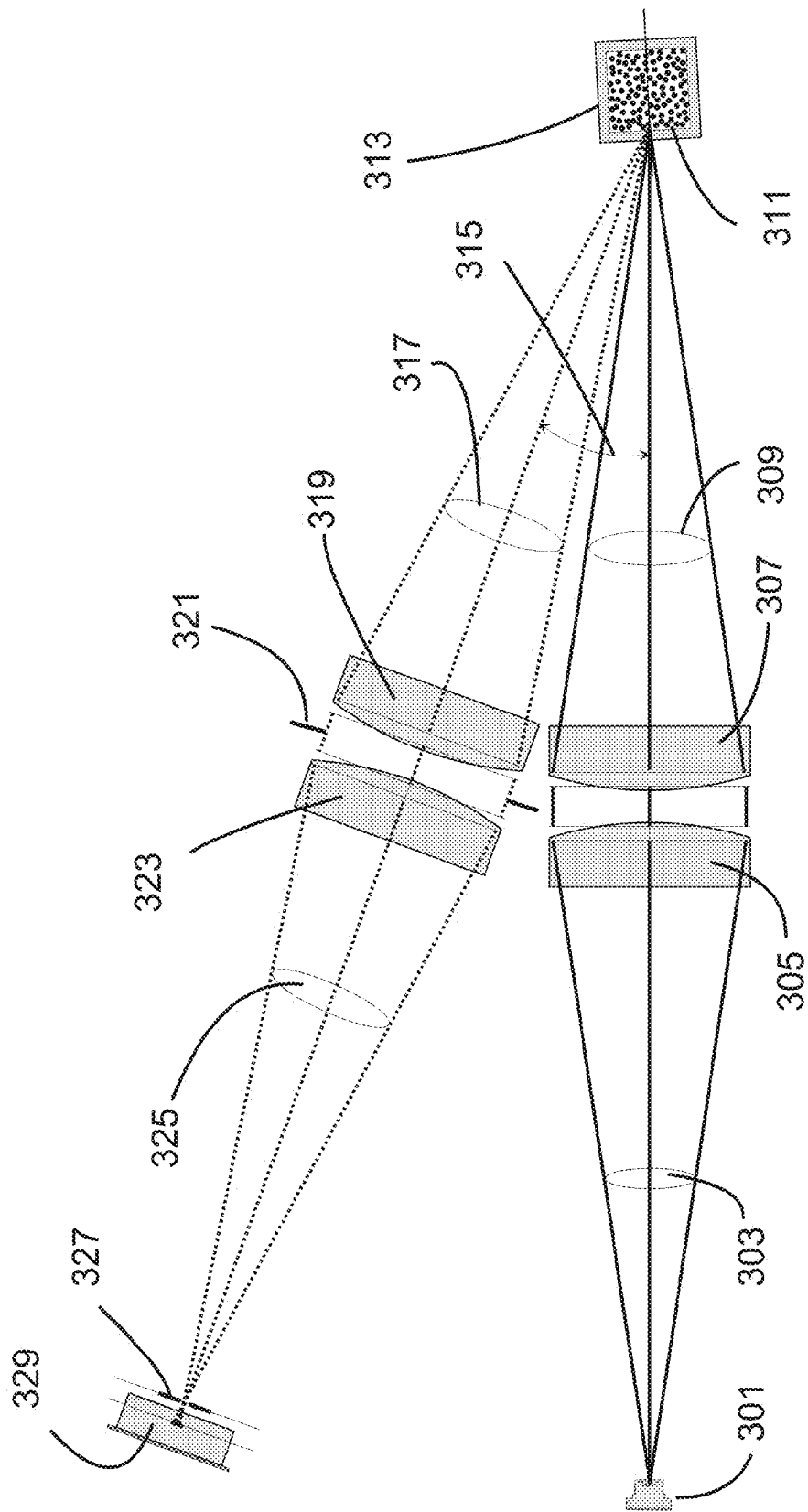
Figure 3 Optical Configuration for Small Matched Field.

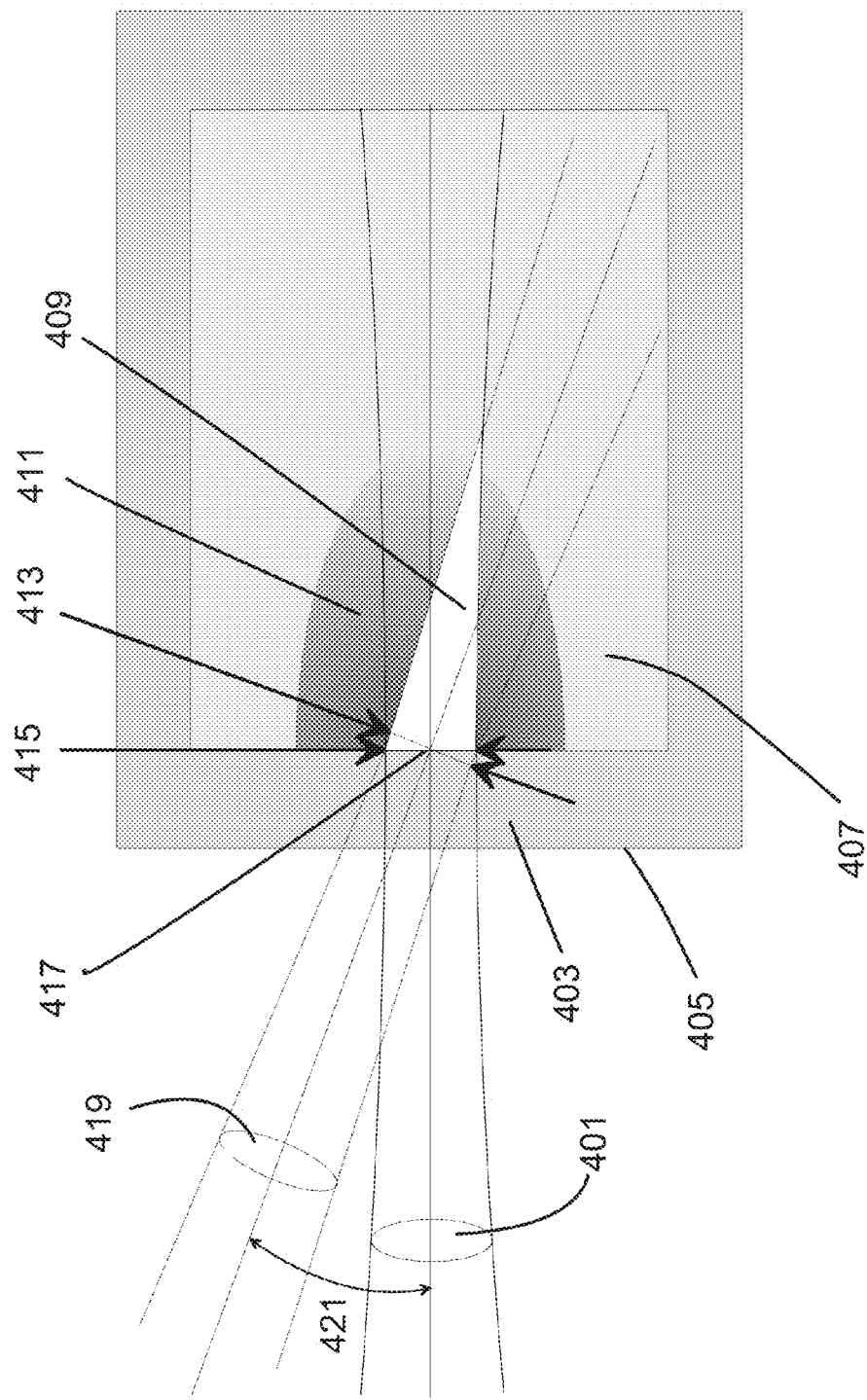
Figure 4  Small Matched Field with Zero Penetration and Rectangular Cuvette

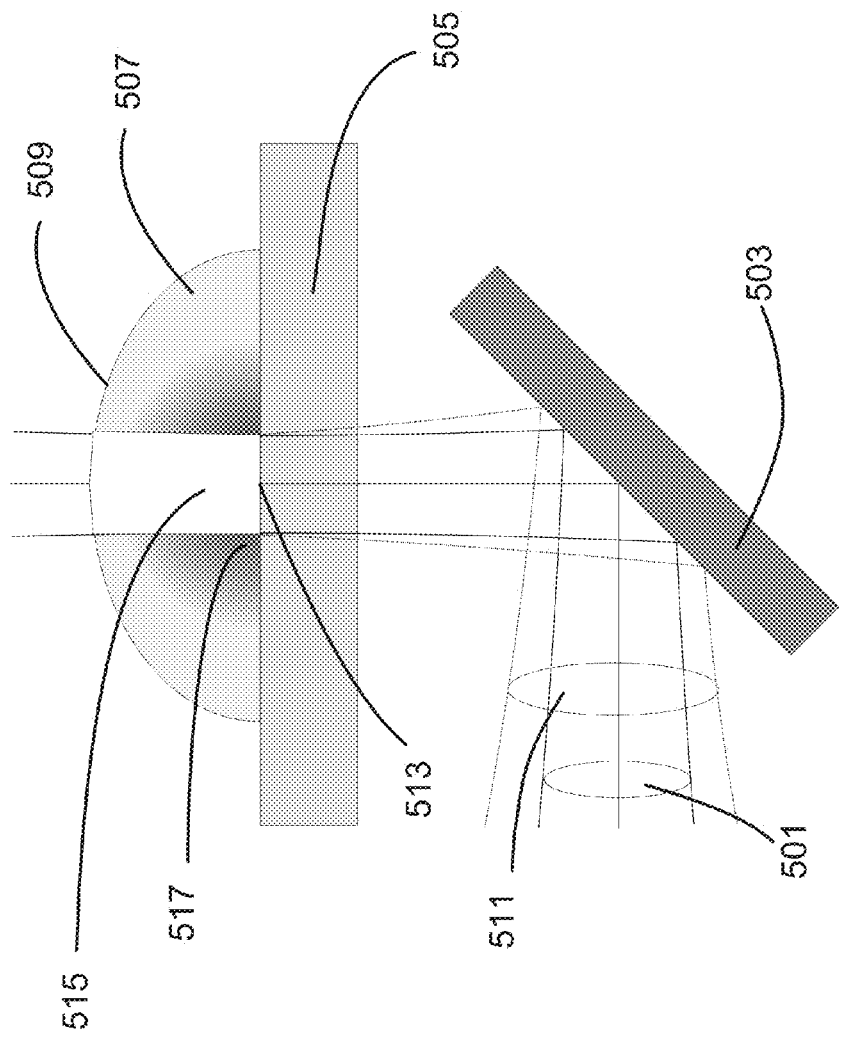
Figure 5  Small Matched Field with Sessile Droplet Specimen

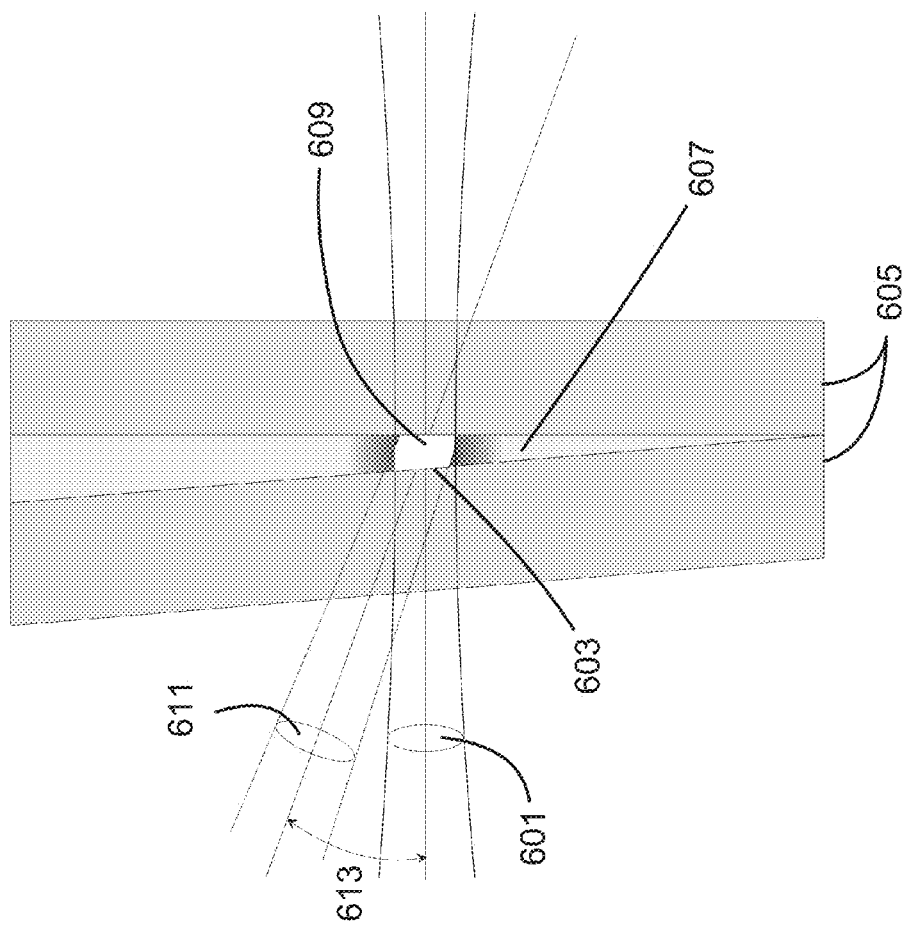
Figure 6  Small Matched Field with Wedged Specimen Chamber

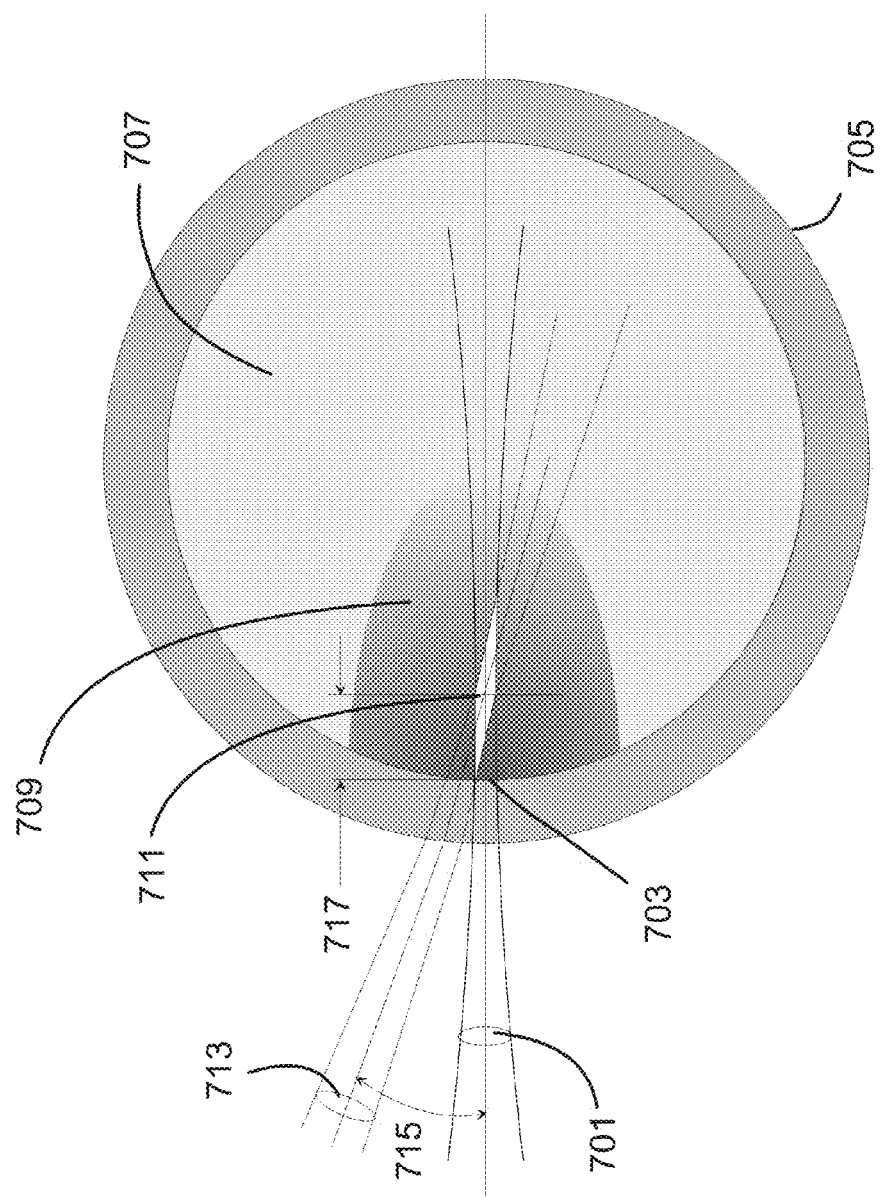
Figure 7 Small Matched Field with Penetration into Circular Vial

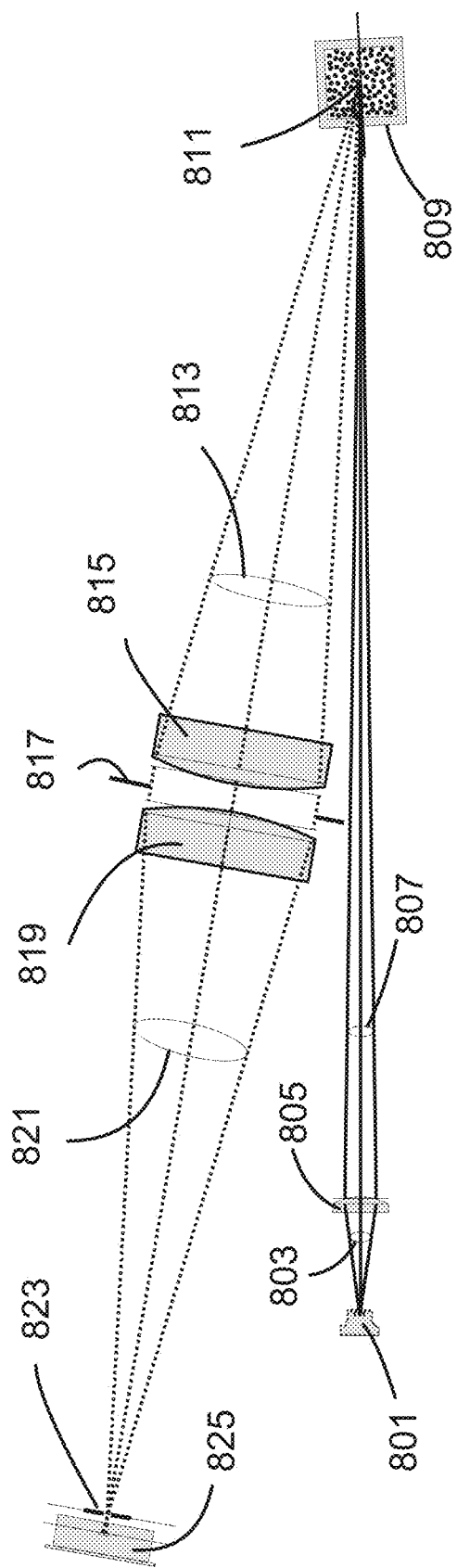
Figure 8 Large Field and Aperture

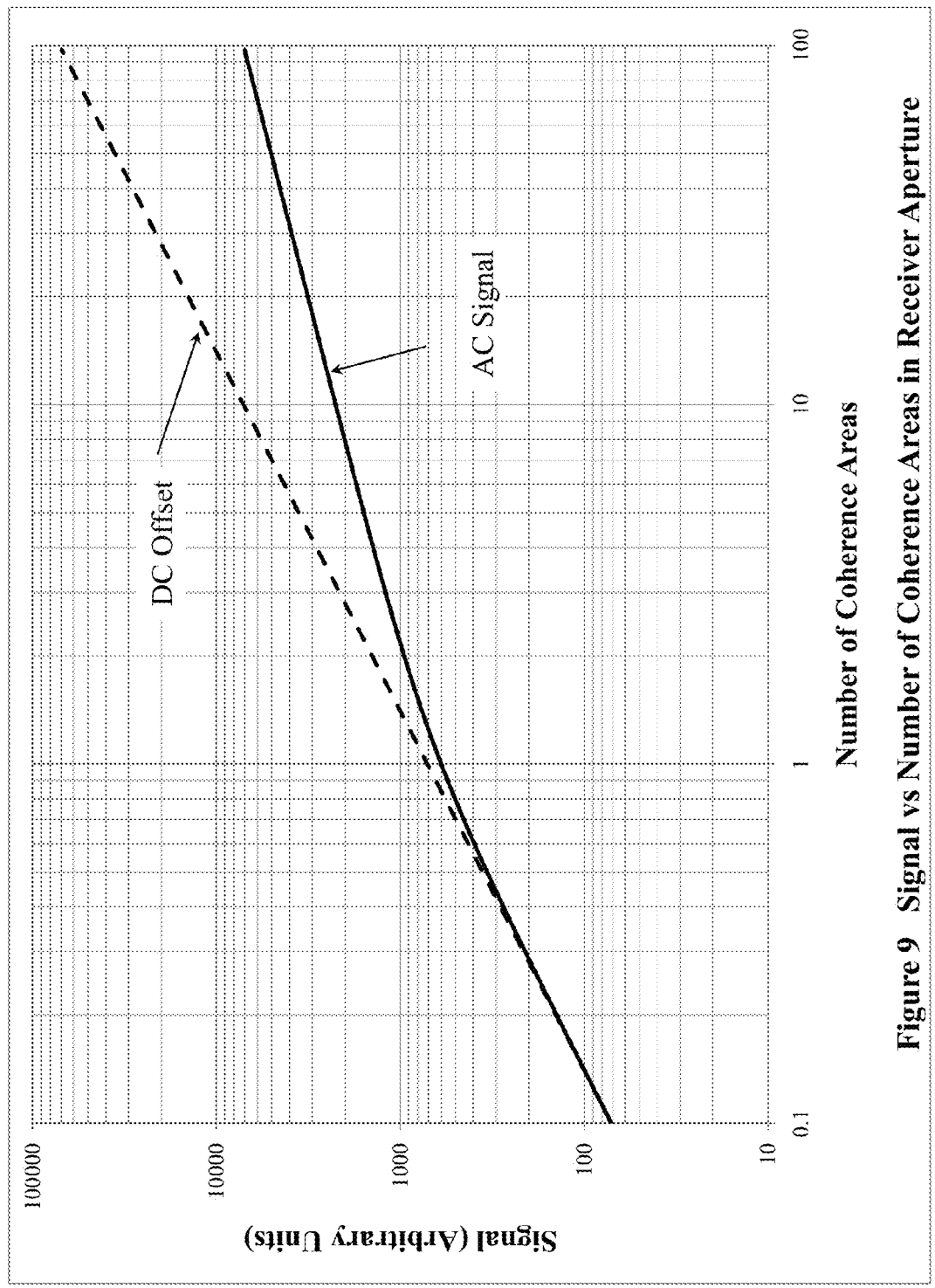
Figure 9  Signal vs Number of Coherence Areas in Receiver Aperture

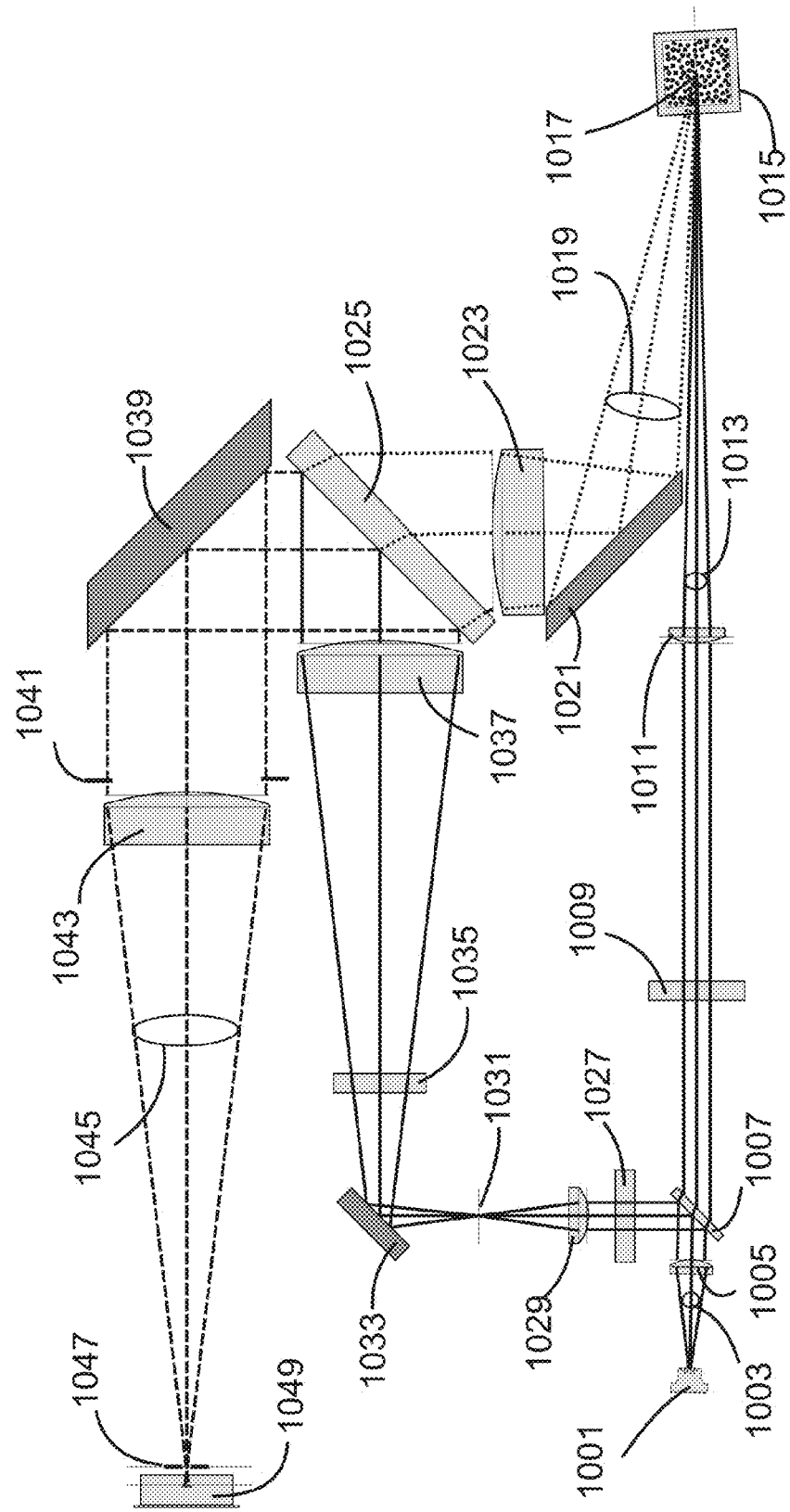
Figure 10 Homodyne Layout

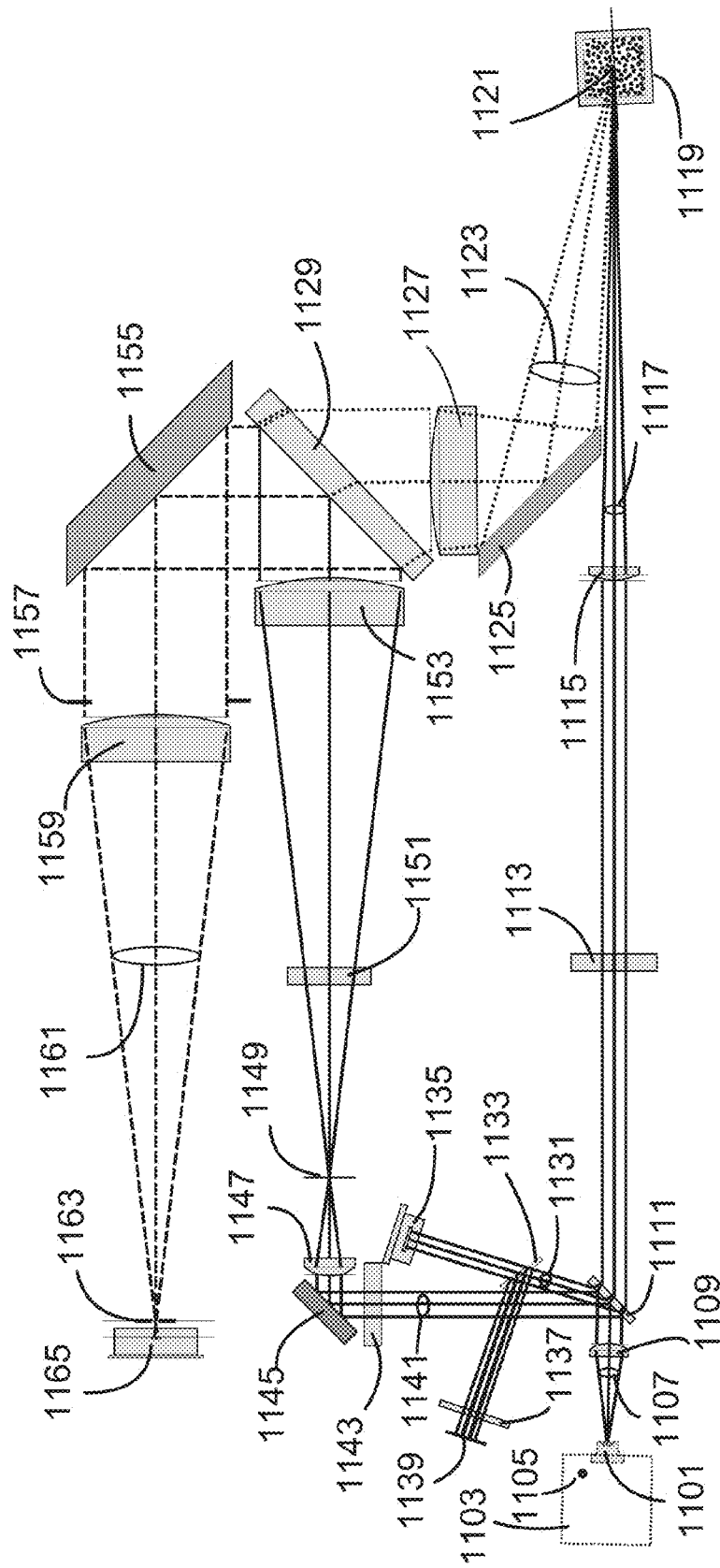
Figure 11 Homodyne Layout with Monitoring

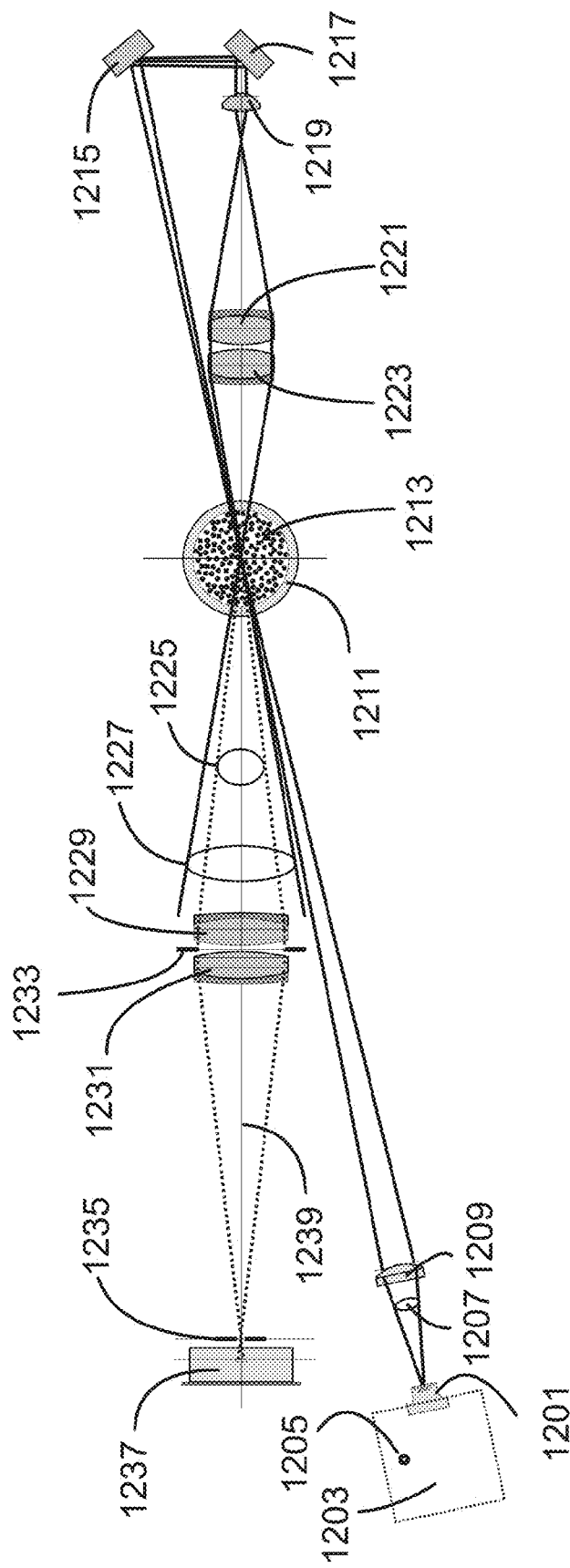
Figure 12 Alternative Homodyne Layout

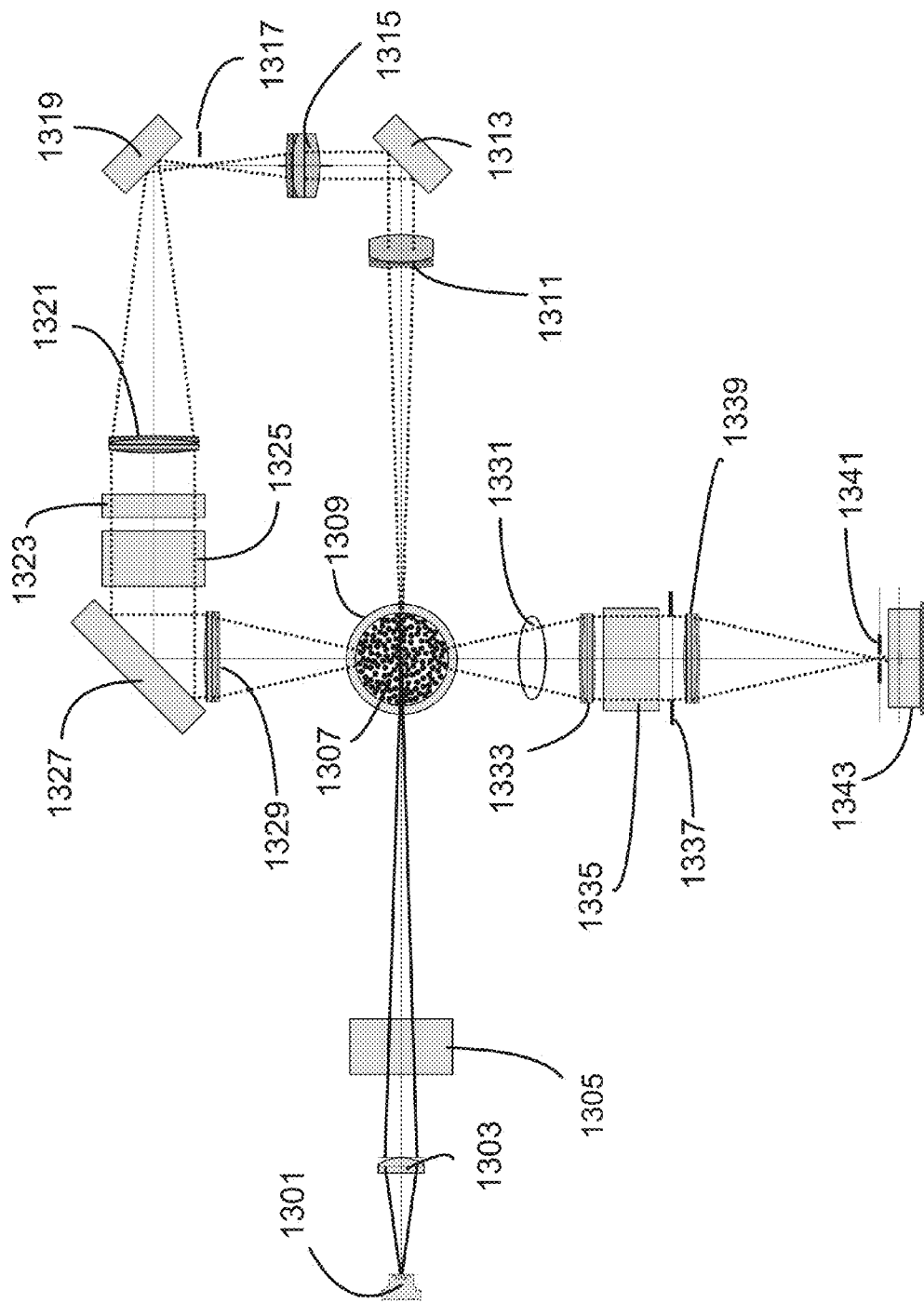
Figure 13 Homodyne Layout for Depolarization Measurements

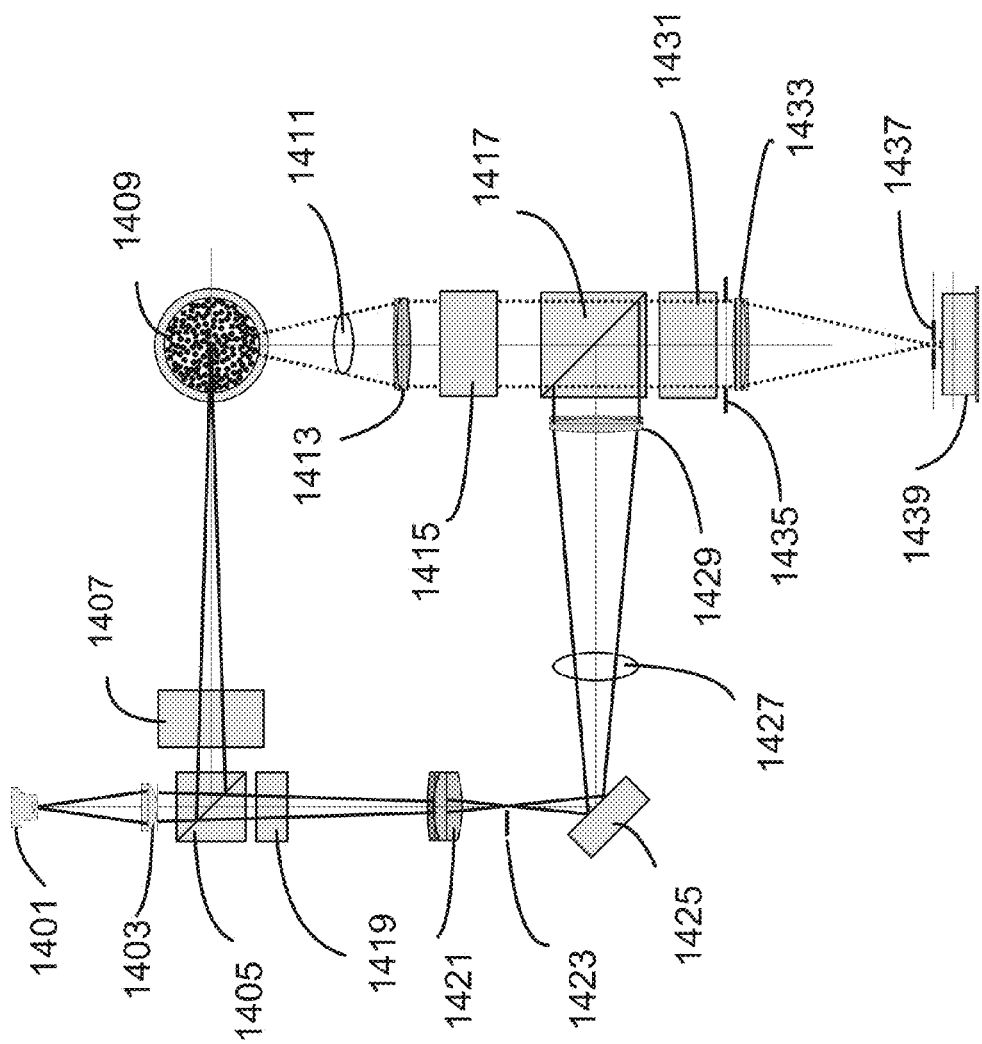
Figure 14  Alternative Homodyne Layout for Depolarization Measurements

DYNAMIC AND DEPOLARIZED DYNAMIC LIGHT SCATTERING COLLOID ANALYZER

RELATED APPLICATIONS

This application is a continuation of U.S. patent application Ser. No. 12/861,079, filed Aug. 23, 2010, entitled "Dynamic and Depolarized Dynamic Light Scattering Colloid Analyzer," by Smart et al., which is incorporated herein by reference.

BACKGROUND OF THE INVENTION

The present invention relates to the field of optical measurement and characterization of a variety of types of particles suspended in a fluid. In particular, methods and apparatus are described for extending conventional boundaries of particle hydrodynamic radius measurement to both higher and lower particle concentration, and further for extending depolarized dynamic light scattering capabilities used for shape assessment.

Dynamic Light Scattering (DLS) is used extensively in research laboratories and elsewhere for the development of new materials and processes, and less commonly is used for process monitoring and control. Commercial applications exist in several industries, including but not limited to: pharmaceuticals (small molecules and protein therapeutics), medical diagnostics (histology, bodily fluids, cataracts), consumer products (personal care, cosmetics, paints, detergents), chemicals, environmental monitoring and remediation (particulate and biological pollutants, oil spill cleanup), advanced materials (powders, coatings, surfactants), and microelectronics (planarization slurries, thin films). Depolarized Dynamic Light Scattering (DDLS) is similar to DLS, but uses polarization techniques to assess deviations from particle sphericity.

DLS relies on the detection of the Doppler shift of coherent radiation scattered from small colloidal particles suspended in a transparent liquid and undergoing Brownian motion, whose behavior depends upon their hydrodynamic radii and/or shape. DLS is commonly used for determining the translational diffusion coefficient of macromolecules such as proteins and polymers, as well as that of larger colloidal particles, typically up to several microns. Because the hydrodynamic radius of a spherical particle may be determined simply from its diffusion coefficient (and the viscosity of the suspending liquid), dynamic light scattering has become the method of choice for characterizing colloidal particles. The phase and frequency of light scattered from many particles is detected as a fluctuating intensity in the far-field as the suspended particles diffuse. DDLS acquires information about the rotational diffusion coefficient of the particles, which depends on the particle size and shape, and may be extracted by suitable mathematical techniques from the fluctuating intensity of the depolarized detected light.

DLS is a preferred measurement technique for the thermally driven diffusion coefficient of particles in suspensions appearing translucent, those with an extinction length from a few millimeters to a few meters. The extinction length, based on Beer's Law, is that distance from the entrance into a medium to where the propagating beam intensity has declined to $e^{-1}$ of its incident intensity. However, several important application areas are outside these traditional limits of DLS. For example, there is great interest in measurement of suspensions approaching opacity, as in process monitoring of high concentration slurries. As the concentration of particles in a suspension increases, the opportunity for scattered light to scatter from more than one particle before arriving at a detector also increases. The resultant multiple scattering statistically yields a higher frequency signal and, consequently, a falsely low measurement of radius. At the opposite extreme, there is also strong interest in the measurement of highly transparent suspensions, such as for environmental monitoring and for characterization of dilute suspensions of nanoscale particles and proteins that scatter very little light. To date, technical solutions to measure accurately in both these regimes remain unsatisfactory.

DDLS has not yet become a popular method for measurement because depolarized signals are typically weak and therefore often obscured by interfering signals such as stray light, optical imperfections, or other system noise sources. In addition, depolarized time correlation functions often decay many times more rapidly than those of DLS, especially for small particles. Increased frequency and reduced signal both present challenges for typical detectors and their following electronics. Typical photodetectors optimized for weak signals, e.g., photomultiplier tubes, also suffer from dead time, after-pulsing and noise problems that arise from detecting a small number of photons per correlation time of the relaxation process.

BRIEF SUMMARY OF THE INVENTION

The present invention introduces techniques and alignment procedures applicable to an apparatus for the extension of Dynamic Light Scattering (DLS) and Depolarized Dynamic Light Scattering (DDLS) for characterizing (e.g., determining particle size, size distribution, and/or particle aspect ratio) colloidal suspensions of particles into concentration regions where conventional measurements are currently difficult or impractical. The first region includes concentrated turbid suspensions that frequently appear visually opaque, and where excessive multiple scattering typically may give a falsely low estimate of particle size. The second region is the opposite extreme where insufficient signal is available to determine the rotational or even the translational relaxation time of the particles, typically when particles are too small, too few, have insufficient refractive index difference from the suspending liquid, or where only the depolarized component is of interest. Separately or in combination, aspects of this invention improve both accuracy and the application range of DLS, and also extend DDLS to formerly inaccessible regions. The invention and its subsidiary aspects described below enable an effective apparatus to be implemented more simply than many others, allowing such possible configurations as a remote probe for process control in hostile environments, accurate characterization of extremely low volumes of specimen, measurement of specimens presented as a droplet on a transparent flat surface, or contained within circular vials or other shaped cuvettes or capillaries, with improvements of accuracy of measurement of particle hydrodynamic radius, polydispersity, and deviations from sphericity, together with prediction of expected error boundaries, and other desirable advantages. While many DLS and DDLS instruments require digital single photon detection with either photomultipliers or expensive avalanche photodiodes (APD) to achieve their performance, here we offer methods of using analog detection with conventional APD or silicon diode photodetector operation to obtain excellent measurements.

BRIEF DESCRIPTION OF THE DRAWINGS

FIG. 1 is a plot of the operational regions of the invention, exemplifying the approximate boundaries of particle size and concentration for DLS/DDLS using the present invention. This exemplary sketch is for 168° backscatter, a visible volume of approximately 1 nanoliter and a particle to liquid differential refractive index of approximately 1.2.

FIG. 2 is a system diagram, showing the modules that constitute a device used to make DLS/DDLS measurements.

FIG. 3 shows the illuminating and detection optics for a Small Matched Field configuration.

FIG. 4 shows a magnification of the configuration geometry of a Small Matched Field centered at the plane entrance face of a colloidal specimen in a rectangular container.

FIG. 5 shows the Small Matched Field configuration with a sessile droplet.

FIG. 6 shows the Small Matched Field configuration with a wedged specimen chamber.

FIG. 7 shows the Small Matched Field with penetration into a circular vial.

FIG. 8 shows the illuminating and detection optics of a Large Field and Aperture. One aspect of the present invention shows an illuminating cone of a much smaller angle than the receiving cone. The now larger diameter of the field stop may match the illuminated diameter at focus, or it may be somewhat larger to observe a greater length of the beam focused well within the colloidal suspension, which may have any of the geometries shown in FIGS. 4 through 7, or otherwise.

FIG. 9 shows an exemplary plot of Signal versus Number of Coherence Areas in a receiver aperture, illustrating a typical signal gain obtained by increasing the collection solid angle from well below (0.1) a conventional single coherence area to many such coherence areas (100).

FIG. 10 shows a Homodyne configuration, where a coherent light source emission surface, a scattering plane, a local oscillator image, and a receiver field stop are all optically conjugate, but not necessarily of the same radius.

FIG. 11 shows a Homodyne configuration with monitoring, extending FIG. 10 to show apparatus whereby light source coherence and/or intensity may be monitored during an experiment.

FIG. 12 shows an alternative Homodyne configuration, where a more compact and simpler method of providing a local oscillator as in FIG. 10 is enabled by a double pass through a specimen, while preserving coherence over a receiver aperture.

FIG. 13 shows a Homodyne configuration for depolarization measurements, again exploiting the double pass approach of FIG. 12, but here drawn with a 90 degree scattering angle for illustration purposes. The operation allows for amplification of either polarized or depolarized scattered light, permitting measurements of both translational and rotational diffusion.

FIG. 14 shows an Alternative Homodyne configuration for depolarization measurements, again shown at 90 degree scattering angle for purposes of illustration.

DETAILED DESCRIPTION

To maximize the measurable range of particle and particle suspension characteristics, such as particle radius, aspect ratio, and concentration, under a variety of empirical constraints, several optical arrangements are presented. The applicable ranges of these arrangements are sketched in FIG. 1, which is a diagram based upon numerical predictions and approximate empirical verification of regions of performance capabilities accessible with the present invention. The abscissa covers a range of fractional volume concentration of particles suspended in a liquid, from 1 part in $10^8$ up to levels limited by the maximum feasible packing fraction. The ordinate covers a range of particle radii from 1 nm to 10 microns, rather larger than the conventionally accepted and typically more limited range of DLS. This exemplary figure is calculated and drawn for near-backscatter conditions (nominally 168°), for a particle-liquid differential refractive index of about 1.2 (polystyrene latex spheres in water), a visible sensing volume of about 1 nanoliter, a coherent illumination of about 30 mW at 658 nm wavelength, and a collection solid angle of about 0.0034 steradians, or less where the signal would otherwise overload the detector, typically towards the upper right of the figure. This diagram shows several important regions of interest, assuming plausible characteristics of a suitable detector and system noise from all sources. The region at the upper left (labeled 'Too Few Particles') corresponds to where the sensing volume contains an average of one particle or less. Although having less than a single particle present does not necessarily prevent measurements, the experiment time increases rapidly and the intensity fluctuation, caused by particles leaving and entering the volume, can introduce errors. The region at the lower left (labeled 'Not Enough Signal') corresponds to a region where scattered light is inadequate to exceed system noise at a probably unduly pessimistic signal-to-noise ratio of unity. In the region at the upper right (labeled 'Multiple Scatter') significant underestimates of the particle size arise from light being scattered more than once before detection. The central bright region (labeled 'Analog Backscatter DLS') covers a rather benign space where good data may be obtained without undue experimental difficulties by any of a number of pre-existing techniques, although toward the edges of even this region increased care becomes essential.

In the remaining regions the range of measurements can be substantially improved using one or more aspects of the present invention and this applies both to DLS and DDLS. The region labeled 'Small Matched Field' may be measured with reduced multiple scattering errors by matching the diameters of the focus of the illuminating beam and the field stop image. This is referred to as "Matched Field." Reducing the diameter of the illuminating beam focus and the field stop image, typically to less than the order of the extinction length, is referred to as "Small Matched Field." In the region of FIG. 1 labeled 'Large Aperture', the receiver, which in prior implementations is conventionally restricted to less than one or, less commonly, only a few speckles, or coherence areas, as determined by the van Cittert-Zernike criterion, here estimated to be about $7.6e^{-6}$ steradians, is increased to include many speckles (about 200 for this figure). This is referred to as "Large Aperture." Measurement in the region labeled 'Homodyne' is achieved by coherently mixing the scattered light with a coherent sample of the light source as a homodyne amplifier.

To summarize, FIG. 1 shows how the measurement range may be extended with several optical configurations: 1) matching the illuminated and visible volumes (Matched Field), the restriction to a field small compared with the extinction length (Small Matched Field); 2) a receiving aperture typically larger than a single speckle (Large Aperture); and 3) coherent homodyne amplification of the scattered signal (Homodyne). Note that the boundaries of the various regions are approximate and created assuming analog detection, typically with an Avalanche Photodiode Diode. The use of photon counting instead of analog detection can move the useful regions of the system down and to the left, with consequent detriment to performance in the upper right.

Many applications of DLS and DDLS use photon counting rather than analog detection. Although photon counting can typically move the useful regions of the system down and to the left, measurements are seriously compromised for light levels leading to quantum detection rates greater than a few MHz. Note that the sharply drawn boundaries are, in fact, rather arbitrarily chosen levels of gently sloping functions of complex parametric variables.

FIG. 2 is a diagram of a DLS/DDLS colloid analyzer system. An Optics Module 201 may contain various optical components that may include but not be limited to, coherent light source, detector, lenses, detectors, apertures, shutter, mirrors, and polarizing components, and a container for the colloidal sample or specimen. A Coherent Light Source Module 203, within the Optics Module 201, produces coherent light with suitable geometrical properties and brings it to the Sample Module 205. The Coherent Light Source Module may consist of a coherent light source and collimating and converging lenses used to transmit and refract light that is presented to a colloidal specimen in 205; in some embodiments it may also contain polarizing components, beam splitters, and/or mirrors or other necessarily or desirable components. Light source wavelength, power, emission geometry, and coherence properties are design options. In one embodiment of the invention, the coherent light source may be a semiconductor laser (e.g., a Hitachi ML 120G21 laser); alternative embodiments may include other types of lasers, e.g., gas, other solid state, etc. In one embodiment of the invention, the lenses may be plastic (e.g., a 302-0380-780 from Optima Precision); alternative embodiments may include lenses of glass or other materials of various optical and mechanical designs.

Coherent incident light 211 emerging from the Coherent Light Source Module 203 enters the Sample Module 205, consisting of an adjustable support structure for the specimen container, which may be one of several different geometries, e.g., a rectangular cuvette, circular or other shaped vial, wedge, capillary or droplet, or other method of presenting a free or constrained colloidal specimen. In some embodiments of the invention, the Sample Module may also contain lenses, mirrors, beam splitters, and/or polarizing components. In one embodiment of the invention, the Sample Module consists of replaceable or substitutable specimen holders, which may comprise stationary or translatable slots for specimen containers of different geometries and/or optical configurations/components. Variable position settings, consistent with translatable slots, optimize light penetration into the colloid specimen. In another embodiment the Sample Module is a permanently placed specimen holder. In still another embodiment, the Sample Module may be a specimen contained outside the instrument, as might be appropriate for in-line or in-situ measurement on a manufacturing line. In another embodiment, the specimen holder may contain a large number of specimens, which may be automatically presented in sequence, with appropriate selection of ideal operating conditions for each.

Scattered light 213 from the specimen enters the Detector Module 207, whose function is to transmit to the detector light scattered from a well defined region of the specimen contained in the Detector Module 207. It contains converging and diverging lenses, aperture and field stops, and a detector; in some embodiments it may also contain other optical elements, such as polarizing components, beamsplitters or attenuators. The aperture stop controls the amount of light incident upon the detector; a larger aperture increases the amount of light detectable from weakly scattering specimens, such as small particles and/or low concentrations and/or small differential refractive index. The field stop, together with scattering angle and any confining geometry, defines the visible sensing volume. In one embodiment of the invention, the detector may be an avalanche photodiode, e.g., a PerkinElmer C30950E detector, converging and diverging lenses in the detector module may be Part #22.1127 from Rolyn Optics, or other suitable components. In one embodiment of the invention, several different aperture stops may be interchanged, for example by placing them at different circumferential stations on a rotating wheel, or in a sliding plate.

In another embodiment of the invention, a portion of the light from the Coherent Light Source Module 203, homodyne light 215, is directed through the Homodyne Module 209. The Homodyne Module may contain several optical components, such as lenses, mirrors, shutters, attenuators and polarizing components, which deliver and control the amount and geometrical configuration of coherent homodyne light incident 217 entering the Detector Module 207, where it is coherently combined with the scattered light 213 from the Sample Module 205 in a beam combiner, now included in the Detector Module. Homodyne light can amplify low intensity scattered signals, increasing the signal-to-noise ratio, to suppress the significance of unwanted optical flare, reduce measurement time, and simplify analysis when multiple particle sizes are present.

The detector contained in the Detector Module 207 converts light to an analog electrical signal 219, which is transmitted to a Hardware Correlator or Data Acquisition Board 221 for processing and analysis. Processing may consist of correlating the acquired signal 219 to obtain a function from which particle translational and/or rotational diffusion properties may be derived. Several signal processing options are possible of which two are: 1) hardware correlation, where a specially programmed device (e.g., FPGA or DSP chip or other microprocessing engine) processes the signal in real time to create a small file of the correlation function that is relayed to the General Computer; or 2) the raw signal is digitized by a Data Acquisition Board, or streamed through the hardware correlator, to the General Computer for archive recording. This archived file may be processed immediately or later with more versatility by one or more of a number of different methods. Later computer processing of archived raw data permits the flexibility of different signal processing options, such as software correlation, or other techniques operating differently on identical data. The results may be compared and process choices later optimized, which is not possible with the real-time non-conservative compression of raw data implicit in correlation. Processed or raw data 225 from the hardware correlator/data acquisition unit is presented to the General Computer 223 for computational analysis to determine particle size, size distribution, aspect ratio, and/or other quantities that can be found from the data. Different embodiments of the invention may include a hardware correlator, data streaming to the computer, or a simultaneous combination of both. Control functions for the correlator from the General Computer or otherwise may also be passed through link 225, as may instructions for reprogramming specific functions or properties of the processing capacity embodied in the Hardware Correlator or Data Acquisition Board.

The Coherent Light Source 203, Sample 205, Detector 207, and Homodyne 209 Modules incorporated in the Optics Module 201, depicted in FIG. 2, are relevant to both DLS and DDLS operational modes. DLS measurements do not typically necessitate the use of polarizing components, as will be evident below, but polarizing components can sometimes improve DLS performance. Polarizing components are necessary for DDLS measurements and must typically be of high quality. Thus, some embodiments of the invention may be used primarily for DLS measurement, while other embodiments are used primarily for DDLS measurements, and still other embodiments are used for both DLS and DDLS measurements.

FIG. 3 shows one configuration of the Optics Module 201, with the illumination and detection configuration for the Small Matched Field. The coherent light source 301 produces an illuminating beam diverging in a cone 303 that is typically somewhat larger than the aperture of the collimating lens 305. (For beams whose intensity profile across any radial section is approximately Gaussian, the boundary of such a cone is defined at the beam half-width, i.e. the distance from the axis at which the electric field drops to $1/e$ of its central peak value, or where a beam's irradiance drops similarly to $1/e^2$. It is convenient here to apply the same criterion even where the beam profile is not truly Gaussian, although other standards exist.) Although overfilling the aperture sacrifices a small amount of light, truncation of the beam by the limb of the lens 305 modifies the light pattern at its focus in the specimen. The circular symmetry of the beam is improved; the effect of intrinsic astigmatism in the light source is partially suppressed, and the intensity pattern at focus marginally more uniform than if the lens is allowed to accept the entire beam, as is the case for the other implementations described in this document, where the light source beam may be wholly transmitted by the aperture stop of the illuminating system. Adjacent to and following the collimating lens 305 is a converging lens 307; together they direct an illuminating beam in a converging cone 309 to a focus in or near specimen 311, here shown contained in an inclined square cuvette 313. The illuminating beam includes both the diverging illuminating cone 303 and the converging illuminating cone 309, which may have the same cone angles, but need not, and is incident on the specimen. The illuminating beam, comprising the available illuminating light, is typically spatially and temporally coherent over the spatial extent of interest in the specimen and other geometrical dimensions of the apparatus. Here and throughout the following sections we follow the convention that 'illuminated volume' refers to the volume within the specimen that receives light directly from the light source, 'scattering volume' refers to the volume within the specimen that is illuminated by the light source AND light scattered by the medium, i.e. multiple scattering, 'visible volume' refers to the volume within the specimen that is visible to the receiving system, whether or not it is directly or indirectly illuminated, and 'sensing volume' refers to the intersection region within the specimen common to the illumination volume and the scattering volume. The diameter of the beam at the collimated section between lenses 305 and 307, focal length of the focusing lens 307 and any residual aberrations, control by diffraction the smallest possible illuminating beam diameter and the intensity contour of the focus within the specimen. A rectangular specimen container, or cuvette, is shown in FIG. 3, but the description suffices for any specimen containment geometry, for which several possibilities are described below, although others may be envisaged. Particles in the scattering volume scatter light into the receiving cone 317, only if it also lies within the visible volume, defined by aperture and field stops in the receiving system. The sensing volume common to illuminated and visible regions is thus optimally constrained to be most sensitive to singly scattered light and least sensitive to multiply scattered light, even though multiple scatter does occur everywhere within the scattering volume. The sensing volume of the specimen 311 is further defined by the receiving optics comprising the collimating lens 319, the aperture stop 321, and the converging lens 323, defining the receiving cone 317, and the field stop 327, the mean scattering angle 315, and the detector 329. Apart from any unwanted stray light from inevitable other properties of all optical systems, the only detected light is that scattered from the sensing volume into the receiving cone 317, whose axis is at an angle 315, the mean scattering angle, to the axis of the converging illuminating cone 309. The solid angle of the diverging receiving cone 317 is defined by the effective aperture stop of the receiving optical system, fairly well approximated by the least diameter of the collimating lens 319, the converging lens 323, and particularly and ideally the stop 321, and its distance from the center of the mean sensing volume. The projected diameter of the visible volume is controlled by the field stop 327 of the receiving optical system imaged into the specimen by the lenses 323 and 319, which may, but need not, have the same focal lengths as each other. In FIG. 3, the illuminating and receiving beams are shown to be approximately the same solid angle and focused just inside the colloidal suspension. The illumination at focus and receiver field stop image planes are conjugate and radially coterminous at the center of the sensing volume. The diameters of the illuminating beam forming lens 307 and the receiver collection lens 319, which are typically the same, physically constrain the smallest feasible scattering angle 315. An exception may be made if different areas within a common lens are used; a situation less desirable however because of the difficulty of controlling coherent ghost reflections and preventing coherent light from the light source scattering into the receiving aperture from other than the specimen. Scattered light in the converging receiving cone 325 is relayed to a focus at the field stop 327 by a receiver focusing lens 323. The receiving beam refers to both the diverging receiving cone 317 and the converging receiving cone 325, which may, but need not, have the same angles. Scattered light to be detected is contained within the receiving cone 325 projected beyond the field stop 327, where scattered light in the receiving cone 325 diverges on to the surface of a detector 329, typically but not necessarily an avalanche photodiode whose diameter exceeds the diameter of the now diverging beam 325 at the axial location of the detector, which is beyond the field stop. The sensing volume diameter must be as small as possible for minimization of the detrimental effects of multiple scattering. The desirability of matching a diffraction limited illumination beam diameter with the field stop image diameter requires that the subtended solid angle of cones 309 and 317, from lenses 307 and 319, be the same.

The Small Matched Field configuration in FIG. 3 refers to a situation where the illuminating beam and field stop image diameters are both the same and simultaneously small enough at focus to be comparable to or preferably less than the extinction length without physical interference of the lenses. Reducing the radius of the field stop image un-matches the illuminating beam and field stop image diameters, reducing both the visible volume and the light received from the illuminated region, but reducing the singly scattered light disproportionately compared with the multiply scattered light. Increasing the radius of the field stop image also un-matches the beam diameters, increasing the visible volume but analogously increasing the multiply scattered light disproportionately more than that from single scattering (see FIG. 8 for further discussion of these effects). A further extension of this idea is that the extinction length can be loosely associated on a statistical basis with a mean distance before a second scattering, indicating a typical sensing volume dimension for the onset of multiple scattering. Restricting the scattering volume (and consequently the visible and sensing volume, see above) mean radius to be less than the extinction length reduces the errors associated with multiply scattered light, which, if a significant amount is detected, gives a falsely low value for apparent hydrodynamic radius. A further and highly significant advantage is the choice of penetration depth, which may be optimally chosen, also on the basis of extinction length. Empirically, good measurements result when the optical penetration is nominally zero, but a slight increase or decrease in penetration where either less or more of the equivalent geometrically visible sensing volume lies within the specimen can be advantageous for extreme opacity or slightly greater transmission, respectively.

Four specimen containment configurations are considered in FIGS. 4 through 7. A capillary containment is substantially similar to that shown in FIG. 7. In each, the Small Matched Field condition is met when the illuminating beam diameter is equal to the field stop image diameter. These specimen configurations can also be used for the Large Aperture and Homodyne configurations, referred to in FIG. 1.

FIG. 4, in one aspect of the present invention, shows an illuminating cone 401, transmitted through an input wall 403 of rectangular containment geometry (cuvette) 405, into a specimen 407. The sensing volume 409 is the region as formerly defined in which the illuminating beam 401 intersects the visible cone 419, but may also include multiply scattered light from the whole scattering region which includes 409 and 411. The location 417 at which the midpoint of the illuminating beam diameter 415 and the midpoint of the field stop image diameter 413 meet, which is also their mutual point of best focus, defines the penetration depth, shown here in FIG. 4 as 'zero', at the inner face of the cuvette. The volume 411 is illuminated by multiple scatter, but is outside the sensing volume 409 that may also contain particles that contribute to multiple scattering. The visible cone 419 is inclined to the axis of the illuminated beam 401 by an angle 421, the mean scattering angle. Note that although it is not shown in this figure, the symmetry axis of the cuvette must be inclined slightly to the normal to the diagram to prevent reflection from any normal surface from introducing destabilizing feedback into the light source. This condition must also be retained in all other methods of specimen containment.

In a colloidal medium, extinction length is a convenient quantitative description of turbidity, and may vary from tens of meters in a visually clear liquid, to a few millimeters for a milky appearance; less than this appears highly opaque. If the extinction length is significantly less than the distance the sensing volume 409 extends into the specimen, multiple scattering can introduce errors. To minimize multiple scattering errors, in one embodiment, the sensing volume 409 should be as small as possible, but consistent with containing enough scattering particles and allowing adequate transmission to and from significant numbers of particles.

The penetration depth into the specimen may be adjusted to optimize the scattered light signal and the simultaneous reduction in the amount of light detected from multiple scattering. In one embodiment of the present invention, this adjustment may be performed via axial translation of the specimen. An example of a device for translating the container that confines the specimen is a manually or electrically controlled micrometer. When in its chosen location, the specimen must be rigidly stationary with respect to the apparatus. Optimization of the scattered light signal includes the largest signal compatible with rejection of multiple scatter and other parasitic effects, such as coherent and incoherent stray light from any and all sources. Ray tracing and geometrical compensation for each specific experimental case allows optimization for different specimen opacities. In the case of translucent colloids, the primary intensity loss is by scattering away from the incident direction. Note that in the configurations of FIGS. 3 and 4, light that is scattered from more than one particle outside the illuminated volume is preferentially outside the visible cone 419 of the receiver, with this condition improving as the extinction length becomes larger compared with the incident beam diameter 415 and the field stop image diameter 413, which are conjugate and coterminous at the intersection plane. FIG. 4 shows a conventional arrangement using a rectangular cuvette with minimal penetration, shown with an intersection point 417 at the cuvette wall, allowing for the best rejection of multiple scatter from scattering region 411. In practice in this and analogously related configurations, the specimen container is inclined out of plane to prevent any light reflected from the entrance surface from entering the receiver cone. Surface contamination should also be minimized as a source of stray light, which can yield errors if its detected intensity is significant compared with the detected scattered light.

For extreme turbidity, where the extinction length is less than the sensing volume diameter, zero penetration of the intersection of the light source and visible axes is optimal for the minimization of multiple scattering effects. Less than zero penetration, where the intersection point is outside the medium with only a small volume common to illumination and visible cones, may be useful to reduce signal overload at the detector. This situation, however, may or may not further improve the effects of multiple scattering, which are essentially controlled by the matching of the illuminating beam and field stop image diameters at their overlap, but can also depend upon the scattering properties of the specimen. Where the intersection point is within the medium, for penetration greater than zero, the signal intensity at the detector can increase. This condition is favorable as turbidity reduces, but improves no further once the visible volume is wholly within the specimen. Further penetration can reduce signal both from increasing optical aberrations and greater attenuation, but may be desirable for highly transparent media where being further away from any scattering from surface imperfections at the vial helps to reduce the effects of coherent flare on the now much reduced signal, which could cause an apparent increase of up to a factor of two in measured particle radius.

FIG. 5, another embodiment of the present invention, shows the Small Matched Field configuration for a sessile droplet specimen. Incident light in the illuminating cone 501 reflects off mirror 503, is transmitted through horizontal flat plate 505, and enters specimen 507. The upper boundary 509 of the specimen defines the thickness and shape of the droplet. The visible cone 511, inclined to the axis of the illuminating cone 501, lies out of the plane of the diagram in FIG. 5 at the scattering angle, and the plate 505 is slightly inclined to eliminate reflection, either back into the illuminating source where it would cause destabilization, or into the receiving cone where it would appear as excess noise or coherent flare. The illuminating beam diameter and the field stop image diameter, not explicitly labeled, are of equal size for the Small Matched Field and are depicted at the entrance face to the droplet. The position of the intersection of the beam diameter and the field stop image diameter is adjustable, and is shown here at location 513, the border of the specimen 507 and flat plate 505. FIG. 5 shows the sensing volume 515 traversing the entire specimen and 517 as the region outside the sensing volume that could contribute to multiple scattering. The illuminating beam enters the specimen from below in FIG. 5; in other embodiments of the present invention the illuminating beam may enter the specimen at the upper boundary 509 of the specimen, or otherwise.

A sessile droplet specimen for DLS/DDLS has several advantages. The specimen can be deposited onto the flat surface 505 via a pipette, minimizing cost and labor associated with specimen container purchase, operation, disposal, cleaning, or contamination. Minimal specimen volume is required for measurement of droplet specimens, reducing specimen material usage and waste. Flat surface 505 may be an inexpensive microscope slide, which can simply be discarded after each use, or cleaned for reuse if appropriate.

FIG. 6, another embodiment of the invention, shows a wedged specimen chamber. The illuminating beam 601 enters a face 603 of the wedge, which consists of two inclined transparent flat plates 605 containing specimen 607. The sensing volume 609 is controlled by the local wedge separation via translation of the wedge and the dimensions of the field stop image diameter, not shown. FIG. 6 indicates the wedge in an upright position, where translation would be in a vertical direction. Alternatively, the wedge may be configured to lie horizontal, where translation would be in a horizontal direction, with the specimen contained by sidewalk, capillary attraction, or otherwise. More generally, the wedge shaped container is translatable to vary the sensing volume depth across the wedge. The wedge may be translated horizontally, vertically, or a combination of both. An example of a device for translating the wedge is a manually or electrically controlled micrometer. When in its chosen location the specimen must be rigidly stationary with respect to the apparatus. The mean axis of the receiving cone 611 is at an angle 613 with the axis of the illuminating beam. Although the scattering angle is shown in the plane of the wedge angle, it could also be inclined at right angles or at any other angle if convenient. In the Small Matched Field, the diameters of the incident beam and field stop image, not depicted, are equal at the point of intersection of their axes, which is shown in FIG. 6 as being close to the middle of the wedge. Penetration is less important here than in the cuvette configuration because the sensing volume 609 typically encompasses the entire distance through the specimen, which is varied in thickness by translation of the wedge along the direction of its taper. In principle this allows a sufficiently thin slice of specimen to be less than the extinction length.

The wedge is cheap and easy to manufacture, and can thus be a disposable item. Several embodiments of the invention might include: a) different mean wedge thickness to vary the amount of specimen in the container; b) different wedge angle to vary rate of change of thickness with translation; c) coatings on either or both of the inner wedge surface(s) to optimize wetting; d) coatings on either or both of the outer wedge surface(s) to minimize reflection (reducing stray light) or optimize reflection (designing for a local oscillator on either the front or back surface to significantly enhance the signal-to-noise ratio); e) absorbing or reflective coatings on either or both of the inner and outer surfaces of the rear plate, acting as a beam-dump; and f) manual or automated translation of the wedge to vary the sensing volume. This last item provides a distinct advantage over traditional vial or cuvette specimen containment, offering a greater range of measurement capability over suspension concentrations, particle sizes, and differential refractive indices; high concentrations typically require small volumes, whereas large volumes yield greater sensitivity at low concentrations. The simpler optics of the wedge also allows quantitative optimization or customization for specific specimen types.

FIG. 7, another embodiment of the present invention, shows the Small Matched Field configuration for a specimen contained within a circular vial, whose geometry is complex in that cylindrical refraction changes both the sensing volume and the mean scattering angle with both penetration depth (horizontal) and translation (vertical) in the plane of the diagram, particularly if the vial axis is slightly inclined to the normal of the diagram, as is usually required to prevent surface reflections from entering either or both of the illuminating and receiver cones. The illuminating beam 701 penetrates the internal wall 703 of the vial 705 into the specimen 707. The region 709 is a volume outside the sensing volume 711 that may contain particles illuminated by multiple scatter and that may contribute, albeit to a lesser extent, to multiple scattering. The mean axis of the visible cone 713 is at an inclined angle 715 to the mean axis of the illuminating cone 701. The length 717 is the distance between the input wall 703 and the intersecting axes and focal planes of the illuminating and visible cones, the so called penetration. Note that both the optical penetration and the mean scattering angle vary slightly with physical penetration because of refraction at the vial inner and outer surfaces. As with FIGS. 4 through 6, the intersection of the illuminating beam and the visible cone defines the sensing volume 711, but the cylindrical curvature of the inclined input wall complicates the refractive geometry. Ray tracing and geometrical compensation for each specific experimental case allows optimization for different specimen opacities. For example, optical distortions are minimal and sensing volume 711 is maximized when the center of the volume coincides with the axis of the circular vial, making both illuminating and received beams radial to the vial, but this cannot be achieved where extinction length is much less than the vial radius.

Four ancillary observations about variable penetration, variable aperture, and rejection of optical ghosts arise, but not necessarily respectively, from the four geometrical examples in FIGS. 4 through 7, and are further addressed in these descriptions below:

(1) The optimization of penetration, or the axial placement of the common focal planes of the illuminating beam and field stop images from the entrance face of the specimen, is highly desirable for different colloidal opacities. In opaque media, light scattered by particles within a field stop image close to the entrance surface of the scattering medium has less probability of multiple scattering before detection, making it the most effective place for the intersecting focal planes of illumination and observing geometry. For more transparent media, a greater penetration not only increases the sensing volume but mitigates the effect of any surface contamination whose magnitude may now become relatively greater than the amount of light detectable from the scattering particles. Although varying the penetration with the circular vial has the same large advantages as those of the rectangular cuvette, some additional consequences must be accommodated. Scanning the vial with respect to the center of the intersection volume in air, either in the horizontal direction in FIG. 7 or at right angles (vertically in the plane of the diagram), moves the sensing volume and changes both its dimensions and the mean scattering angle because of the cylindrical optical refractive power of the vial wall. An analogous but reduced and simpler effect also manifests in the other examples of specimen containment. Thus allowance must be made for the actual values of mean scattering angle and sensing volume center and dimensions, typically by ray tracing under the local empirically chosen conditions. There can be a small variability of the mean scattering angle, penetration, and aperture with local position within the sensing volume, but this is usually too small to introduce errors comparable with those from other sources.

(2) When the penetration is minimal and where some high-opacity colloids may scatter so much light that the detector may be overloaded, the diameter of the receiver aperture stop may be reduced to prevent excess light leading to detector overload and/or signal distortion. Reducing the illuminating optical power electrically is undesirable, because it may impair the stability of the light source and hence compromise the coherence of the incident illumination. Attenuation by a neutral filter implemented as a glass plate of the order of a millimeter or so thick may also be undesirable because wherever in the beam it is installed, a normal placement can introduce destabilizing feedback from reflection back into the coherent light source, while any inclination to mitigate this changes the alignment geometry. Avoiding these effects by attenuation with a suitably coated and inclined pellicle is both less robust and more expensive. The reduction of a receiver aperture that already contains many coherence areas, while reducing the DC component leading to overload, only reduces the AC component as the square root of the number of detected coherence areas and is thus the most desirable method of preventing overload or signal distortion. This is typically implemented by exchanging receiver aperture stops of different diameters.

(3) Incoherent and unquantified coherent stray light must be kept to a minimum. This implies an uncontaminated specimen, well designed and chosen geometry and surface coatings, and cleanliness and freedom from damage of the specimen containers, particularly where the amount of detected scattered light approaches the noise floor of the system. Rejection of optical ghosts that could permit light reflected and/or refracted by any surface or combination of surfaces in the system into the receiving aperture is absolutely essential. Rejection of ghosts typically to third order may be acceptable, but possibly down to fifth order for certain specimen containers. Tilting the plane of the illuminating beam entrance window to the specimen by about 5 degrees of arc is typically effective as confirmed both by geometrical ray tracing and empirical visual and electronic observation through the detection system. It may not always be possible nor easy to meet this requirement, for example, in the case of the upper surface of the sessile droplet.

(4) Where the scattered signal is small, for whatever reason, unknown amounts of coherent stray light lead to errors—typically giving a falsely large particle diameter by up to a factor of two. However, this may be exploited for certain specimen containment devices and geometries by deliberately introducing coherent stray light in excess of a few tens of times the power of the detected scattered light. This can emulate the homodyne systems described below, and may be useful under certain conditions. The correlogram must now be analyzed as for homodyne to allow for the factor of two reduction in the apparent relaxation time scaling.

FIG. 8 shows another configuration of the Optics Module 201, showing the illumination and detection configuration for a Large Aperture implementation. A coherent light source 801 produces an illuminating beam contained in diverging cone 803 that is smaller than the lens 805, which may have aspherical convex contours, and which focuses the illuminating beam into the specimen. The illuminating cone 807 formed by the lens 805 is of smaller radius and lower convergence rate than the beam formed by the collimating lens 305 and converging lens 307 in FIG. 3, giving a larger focal waist 807, because of diffraction properties, and permitting the illumination of a much greater volume of specimen. The illuminating beam of light incident upon the specimen comprises both diverging cone 803 and converging cone 807. FIG. 8 shows a tilted rectangular cuvette 809 containing specimen 811, but the discussion suffices for other specimen geometries, for example those shown in FIGS. 4 through 7. Some light scattered from the specimen 811, enters the diverging receiving cone 813 whose solid angle is defined by the effective aperture stop of the receiving optical system, fairly well approximated by the least diameter of the collimating lens 319, the converging lens 323, and particularly and ideally the stop 321, and its distance from the center of the mean sensing volume. The diameter of the field stop 823 may now be chosen on the basis of the illuminating beam diameter at the focus, typically but not necessarily to be the same. If it is the same, then this becomes identical with the Small Matched Field implementation, but with an absolute diameter larger than that formerly described—because the converging cone 807 has a smaller angle, leading to a larger diffraction limited diameter at its focus. An alternative embodiment of the present invention comprises an optical configuration of FIG. 3 with a large aperture stop 817. If the field stop image differs from that of the illumination at focus, the system becomes more sensitive to multiple scattering. Where the field stop image diameter is smaller than the illuminating beam diameter, the system becomes less sensitive to total signal because the sensing volume is smaller than before. Where the field stop image diameter exceeds that of the illuminating beam, the system sensitivity increases with the greater sensing volume of the increased visible illuminated intersection length. The focal lengths of the lenses 815 and 819 need not be the same provided that allowance is made for the image magnification between the field stop and its image. Light scattered into the diverging cone 813 is relayed to a focus at the field stop 823 by a receiver focusing lens 819 forming a converging receiving cone 821. Beyond the field stop 823, scattered light continues to diverge at the same cone angle as 821, where it is incident upon the surface of a detector, which must be large enough to intercept the entire scattered beam transmitted by the optical aperture and field stops.

The configuration shown in FIG. 8 is well suited to the measurement of nearly transparent specimens that are not too seriously constrained by multiple scattering, and can be a good compromise to maximize the range of application for different extinction lengths. Of further advantage is the increase of a field stop image diameter to equal or slightly exceed the illuminating beam diameter (neither the field stop image diameter nor the illuminating beam diameters are specifically indicated in FIG. 8). Once the field stop image diameter exceeds the illuminating beam diameter, further advantage may continue to accrue from a larger signal from the now longer sensing volume, more advantageous here because the illuminating beam attenuation is negligible over the distances of interest. The diameter of the aperture stop 817 may now be optimized in terms of the available signal. A final doubling of the scattered light signal is available by translating the entrance wall away from the focal plane so that the entire optical intersection volume lies wholly within the specimen. Under this condition all dimensions of the sensing volume must exceed the extinction length by enough to avoid the detection of any significant multiple scattering—more readily satisfied for highly transparent suspensions.

The logarithmic plot in FIG. 9 quantifies the advantage of the configuration found in FIG. 8 and elsewhere throughout these descriptions, achievable by detecting a number of coherence areas or speckles greater than the conventionally accepted unity, as defined by the van Cittert-Zernike coherence theorem. The collection solid angle in DLS is traditionally restricted to be less than one speckle to get the greatest signal contrast or highest 'intercept' of the autocorrelation function of the detected signal, while satisfying necessary statistical criteria, but at the expense of an unnecessarily small optical signal. Including many coherence areas, while reducing both the contrast in the signal and the proportional intercept of the correlogram, does however give a larger signal.

Although the DC offset increases with the number of speckle areas in the optical aperture, the AC signal rises approximately only as the square root of the number of visible speckles. However this may conveniently be sufficient to overcome other noise sources while preserving and improving ergodic statistical integrity. A formerly supposed disadvantage is that the larger solid angle includes a spread of scattering vectors and so reduces accuracy. However, this may be acceptable for extremely small particles or low levels of scattering where measurements may not otherwise be possible, particularly with the slower variation of the scattering vector with angle in near backscatter. For a given subtended normal radius of the illuminated visible specimen volume, increasing the aperture increases the number of visible speckles. At lower scattering angles, a vertical slit (or mask) can be used to minimize any spread in q-vector value while retaining some of the advantages stated above. The solid angle subtended by each coherence area is proportional to the square of the quotient of the wavelength divided by the field radius of the virtual source at the sensing volume. In FIG. 9, the abscissa represents the number of visible coherence areas, which is proportional to the collection solid angle. The straight dotted line shows the arbitrarily scaled linear increase in DC level with aperture area, whereas the solid line represents the corresponding detected AC signal, showing a linear improvement of signal as the detection area increases up to about a single van Cittert-Zernike coherence area (one speckle), beyond which the signal becomes proportional to the square root of the number of speckles, according to the statistics imposed by the central limit theorem. Note that although the AC/DC ratio falls, the AC signal continues to increase, an advantage not typically exploited by conventional DLS or DDLS systems, but of significant advantage—about a factor of 20 for the example shown in FIG. 9, when the DC is small enough not to overload the detector. While the electrical output signal can be AC coupled, unfortunately this is not possible for the optical input signal, preventing the advantageous gain from being even larger. The figure is sketched from approximations to the rather complex mutual coherence functions and neglects both the diffraction limitation of the optics as small apertures are approached and other optical subtleties, but the major conclusions are not materially affected.

Increasing the aperture is also useful for concentrated suspensions, where the sensing volume is matched to minimize the effects of multiple scatter. The small sensing volume typically used in the measurement of concentrated suspensions gives large speckles and the region in FIG. 9 where the signal gain with aperture begins to increase more slowly than linearly, occurs at a larger solid angle. With high level signals, it is, however, also important not to exceed the permissible illuminating power density at which the specimen might be altered. The implications of this aspect of the invention are at least, but not necessarily limited to, calculation of an optimal collection aperture, and the possibility of obtaining sufficiently more signal to permit an avalanche photodiode detector with analog electronics to replace a photomultiplier with higher speed digital discrimination circuitry, thus avoiding errors such as dead time, pulse-pile-up and other limitations of high-power detection with a quantum realization (photon detection or counting) system. An aperture larger than the typical van Cittert-Zernike single speckle limit can thus be useful where signal level was formerly insufficient, regardless of whether the detection method is analog or quantum-realized. Conversely the reduction of collection solid angle to well below a single speckle carries no penalty where a smaller sensing volume can postpone to higher concentrations the detrimental effects of multiple scatter, while simultaneously avoiding detector overload from the now much more highly concentrated and specimen that may scatter more light.

FIG. 10 shows another configuration of the Optics Module 201, showing an illumination, detection, and homodyne configuration pertinent to the "Homodyne" referred to in FIG. 1. The coherent light source 1001 produces a diverging illuminating cone 1003 transmitted wholly by the aperture of the collimating lens 1005, which is larger than the beam. After the collimated illuminating beam passes through a beamsplitter 1007 and an optional attenuator 1009, a further lens 1011 produces a converging cone 1013 focused to a suitable diameter at the specimen. The illuminating beam, comprising the diverging illuminating cone 1003, the collimated section (not labeled), and the converging illuminating cone 1013 is incident on specimen 1017. The container 1015 for the specimen 1017 is shown as square, but the description suffices for any containment geometry, e.g., as shown in FIGS. 4 through 7, or otherwise. The beamsplitter 1007 may be an uncoated flat glass plate with a wedge angle that may be close to 1 degree of arc, or a little more, with the first surface reflection constituting the homodyne beam. The second surface reflection, not shown, with a comparable few percent of the incident power for an uncoated glass beamsplitter, is inclined away from the first beam to miss the following small lens 1029. The collimated homodyne beam is reflected from the first surface of the beamsplitter and proceeds through attenuator 1027, converging lens 1029, and pinhole 1031, to be reflected by mirror 1033, proceeding then through attenuator 1035 and collimating lens 1037 to beam combiner 1025. Scattered light contained in the visible cone 1019 and reflected by the plane mirror 1021 is collimated by lens 1023 to pass through the beam combiner 1025, where it overlies the collimated homodyne beam arriving through collimating lens 1037 at approximately right angles to the front surface of the beamsplitter 1025. The scattered light and homodyne beam are both reflected by mirror 1039, to proceed through aperture stop 1041 and converging lens 1043. The scattered light and homodyne beam contained in converging cone 1045 passes through field stop 1047 to detector 1049, as described in earlier implementations.

Since the surfaces of beamsplitter 1007 are uncoated, their reflection and transmission coefficients are given for either polarization by the Fresnel equations relating refection properties to wavelength, refractive indices, and inclination angles. It is highly desirable to collimate the beam before transmission through the inclined beamsplitter 1007 to avoid distortion of the focal region by tangential and sagittal astigmatism, inevitable with a flat plate in an uncollimated beam, and yet more detrimental when that plate is not normal to the optical axis. It may also however be useful to allow small optical changes, such as, but not necessarily limited to, deliberate introduction of aberrations to compensate for light source astigmatism, or other properties, of advantage to optimal implementation, and which will be obvious to those well versed in the art.

The beam combiner 1025 is also an uncoated wedged flat glass plate, which in the collimated beams introduces negligible aberrations into the image of the field stop. Its wedge angle, which may be close to 1 degree, is necessary to reject the contribution to the homodyne beam derived from the second or rear surface with respect to the homodyne beam at the beam combiner 1025. This means that that the angular separation of the reflected beams gives the necessary spatial separation of the multiple homodyne source images, conveniently by more than twice the sum of their radii at the field stop plane 1047, where only one beam consisting of a combination of scattered and homodyne beams is transmitted by the field stop 1047. The second surface reflection would otherwise cause a partial overlap of two homodyne beams of not-too-dissimilar intensities, causing fringes that could be smaller than the scattered coherence areas, and hence lower the modulation depth of the signal. It is also necessary to shift any returned image of the rear surface reflected homodyne spot from the (potentially shiny) face of pinhole away from the visible volume, or from the possibility of being accidentally returned to the light source where its effects become complex and detrimental because of potential modulation. The image at the field stop 1047 of the homodyne light reflected from the front surfaces of the beamsplitters 1027 and 1025 is much smaller than the field stop, through which it is aligned to pass. The collimated homodyne beam reflected from the front surface of the beamsplitter 1007 is focused by the lens 1029 to a plane 1033 where its focal diameter is also much smaller than the diameter of the incident beam 1013 in the specimen. The light beam collimated by the lens 1037 is formed to impinge upon the beam combiner 1025 at such an angle that its spatial coherent wave-front perfectly overlies the mean wave-front of the scattered light in the receiving cone 1019. The homodyne beam diameter sufficiently exceeds the aperture stop 1041 diameter so that its intensity is sufficiently uniform for acceptable homodyne gain over the entire aperture, typically with a ratio of better than 2:1. The angles are established such that following the beamsplitter 1025, the nominally flat electric field wave-fronts from both homodyne and specimen are closely parallel. The layout in FIG. 10 permits a more compact implementation of the apparatus than is available where real time monitoring is deemed to be necessary, as shown later in FIG. 11.

To assure the ability to choose optimal absolute and differential intensities of the illuminating and homodyne beams, an attenuator 1009 may be introduced into the collimated segment of the illuminating beam, where it not only avoids the introduction of negative spherical aberration, but also prevents axial translation of the 'disk of least confusion' of the incident beam defining its best focus. The attenuator may be implemented as a simple neutral density filter, of absorptive or reflective type, or as a rotating polarizer or other device capable of tunable attenuation. An analogous but adjustable attenuator 1035 may be introduced for similar intensity control into the homodyne beam, but must not change its apparent optical thickness with transmission adjustment, to avoid axially translating the virtual source point of the homodyne beam, since it is diverging at the station of the attenuator 1035. Even without adjustment such a flat plate in a diverging beam introduces negative spherical aberration, which here has almost negligible detrimental consequences provided that it does not vary with time. For discrete adjustment of intensity by the interposition of attenuating plates 1027 of different thickness, these should be placed where the beam is collimated between the beamsplitter 1007 and the homodyne focusing lens 1029. Since attenuators 1027 and 1035 are functionally equivalent, it is preferable to use only 1027 for aberration control, but this may be less convenient for physical packaging reasons. The orientation of the highly polarized (typically greater than 100:1) illuminating light source beam may be adjusted to provide 'S' or 'P' or other polarization with respect to the plane of the figure, permitting a wide range of adjustment or adaptability of relative intensities by attenuators 1009 and 1027 or 1035, or Fresnel reflection at the beamsplitter 1007, the mirror 1033, or the beam combiner 1025, or otherwise. For small particles, typically in or close to the Rayleigh scattering regime, the polarization orientation of the incident beam does not have a strong effect in near-backscatter, but can be a useful variable for independent control of the relative beam intensities.

To exploit the advantages of homodyne gain, two intensity conditions must be satisfied; (1) the total signal must not overload the detector nor exceed its linearity over a usable range, and (2) the ratio of homodyne to scattered light intensities must be large enough, typically greater than fifty times, to avoid introducing excessive relaxation time measurement errors, which would otherwise arise because the relaxation time without homodyne is typically half that measured with an excess additive coherent field. To satisfy these conditions simultaneously for different amounts of scattering, it is desirable to control the homodyne intensity independently of the illumination of the visible volume.

Many applications provide optical homodyne gain and increase signal-to-noise ratio by mixing with the scattered light a spatially and temporally coherent electric field wave-front derived from the same optical source. The maximum possible theoretical improvement is where the residual noise is the shot noise implicit in quantum detection of the scattered light, but in practice is usually limited by the noise in the illuminating light source. The critical interferometric alignment necessary to assure that mutual spatial coherence is maintained over the receiving aperture may be relaxed to produce a simple and robust apparatus, as described in FIG. 10.

The first salient feature of this homodyne implementation is that the light source emission surface, its focal plane in the medium, the focus of the homodyne beam 1031, and the field stop 1047 are all optically conjugate, although not all illuminated patterns are of the same radius. The second is that the diameter at the focus of the homodyne beam 1031 is much smaller than the field stop 1047 so that small misalignments will not significantly affect transmission by the field stop nor the effectiveness of the wave-front overlap. Typically, for optical homodyne gain, the wave-front match over the common area has a phase disparity of substantially less than $\pi/2$. This remains true if the receiver aperture 1041 contains less than one van Cittert-Zernike area, or more simply but less exactly, a single speckle. Where the aperture contains many speckles, a condition attractive to increase the available signal, the phase match over each coherence area (speckle) has the same $\pi/2$ condition. However, the homodyne phase front need not be constant over the entire aperture provided that it satisfies the coherent interference condition over more than each scattered speckle diameter independently. This relaxation of the interferometric alignment condition is possible because the dynamically random phases of the scattered light from an ensemble of independent particles assures proper temporal modulation, with typically, but not necessarily, Gaussian statistics. The implementation introduced in FIG. 10 allows homodyne light of acceptably uniform intensity and phase coherence over the receiving aperture to be guaranteed with more relaxed and forgiving alignments than conventional interferometric requirements. Even if the $\pi/2$ condition is compromised the detriment to the signal falls only slightly.

Homodyne amplification offers advantage in both low and high concentration applications. First, where the particle suspension is highly transparent and only a small signal is available, because the particles are small, at low concentration, or with a refractive index close to that of the liquid, the homodyne beam may be used to amplify the scattered signal power. By increasing the homodyne beam power, the amplification may be made as large as desired until the light source noise exceeds that of the shot noise in the signal up to the limit of emission noise, beyond which no further improvement is obtained. Even before the onset of this condition, shot noise in the signal may limit the accuracy or even feasibility of experimental measurements. In this first condition of low scattering, the sensing volume may be usefully increased to provide more particles, and the receiving aperture may now be expanded beyond the often accepted single speckle solid angle with advantages discussed elsewhere in this document. Second, for highly concentrated and turbid particle suspensions, the homodyne system offers advantages in entirely different ways. The illumination and receiver matching conditions are necessary as before, but as the volume bounded by the projected area is reduced the sensing volume contains fewer particles, yielding a reduced signal, with potentially changed statistics, as the intensity fluctuation spectrum may distort the phase spectrum indicative of the particle size. Increasing the light source power may increase signal, but because of the small field this raises the intensity or power density, perhaps beyond the damage threshold of the specimen. Homodyne gain is now useful to raise the signal as the sensing volume is reduced beyond formerly accessible limits, but shifts from the conventionally statistically stationary measurement to the equivalent of an intensity fluctuation spectrum, more difficult to interpret but now possible to analyze. A second advantage in this case may be less obvious. At extreme concentration, particles may either stick to the wall or be otherwise constrained in their assumed isotropic Brownian motion. The light from these adds coherently to the desired scatter but changes the apparent relaxation time behavior leading to a false size estimate. With added homodyne this light can be swamped into insignificance with reduction of associated errors up to higher concentrations, typically by the reduction of cross-terms in the scattering matrix.

As is well known to those versed in the art, homodyne amplification has many potential advantages in addition to those presented above. It dilutes and hence reduces the detrimental effects of any coherent, or even incoherent, stray light. It also produces an undistorted measurement even when the statistics of scattered light are not Gaussian, as is traditionally assumed. The only accessible conventional measurement is that of the second order, or intensity, the light source noise exceeds that of the shot noise in the signal up to the limit of emission noise, beyond which no further improvement is obtained. Even before the onset of this condition, shot noise in the signal may limit the accuracy or even feasibility of experimental measurements. In this first condition of low scattering, the sensing volume may be usefully increased to provide more particles, and the receiving aperture may now be expanded beyond the often accepted single speckle solid angle with advantages discussed elsewhere in this document. Second, for highly concentrated and turbid particle suspensions, the homodyne system offers advantages in entirely different ways. The illumination and receiver matching conditions are necessary as before, but as the volume bounded by the projected area is reduced the sensing volume contains fewer particles, yielding a reduced signal, with potentially changed statistics, as the intensity fluctuation spectrum may distort the phase spectrum indicative of the particle size. Increasing the light source power may increase signal, but because of the small field this raises the intensity or power density, perhaps beyond the damage threshold of the specimen. Homodyne gain is now useful to raise the signal as the sensing volume is reduced beyond formerly accessible limits, but shifts from the conventionally statistically stationary measurement to the equivalent of an intensity fluctuation spectrum, more difficult to interpret but now possible to analyze. A second advantage in this case may be less obvious. At extreme concentration, particles may either stick to the wall or be otherwise constrained in their assumed isotropic Brownian motion. The light from these adds coherently to the desired scatter but changes the apparent relaxation time behavior leading to a false size estimate. With added homodyne this light can be swamped into insignificance with reduction of associated errors up to higher concentrations, typically by the reduction of cross-terms in the scattering matrix.

As is well known to those versed in the art, homodyne amplification has many potential advantages in addition to those presented above. It dilutes and hence reduces the detrimental effects of any coherent, or even incoherent, stray light. It also produces an undistorted measurement even when the statistics of scattered light are not Gaussian, as is traditionally assumed. The only accessible conventional measurement is that of the second order, or intensity, correlation function. To obtain the required first order, or field, correlation function from which the Doppler spectrum may be recovered, the Siegert relationship is conventionally assumed, but this relationship is only truly correct for Gaussian statistics. Homodyne amplification makes the first-order correlation function directly accessible and obviates the need for questionable statistical assumptions. Where two or more particle sizes are simultaneously present the cross terms are also significantly reduced, making the recovery of different particle sizes both easier and more accurate. Since the application of homodyne also reduces the measured relaxation frequency by a factor of two, a reduced system bandwidth can similarly reduce noise.

FIG. 11 shows a homodyne arrangement similar to FIG. 10 with the addition of real time monitoring facilities, desirable to assure that at all times during the experimental measurements the conditions were actually as initially and/or finally supposed. As in every example discussed so far, the temperature of the coherent light source 1101 is controlled by a Peltier bismuth telluride thermoelectric stack cooler 1103, which is monitored in a closed loop servo by a thermistor 1105. As in FIG. 10, the illuminating beam is collimated by the lens 1109, and a sample is extracted by the beamsplitter 1111. Beyond this point the remaining illuminating optics, sample module, and detection optics, and even most of the homodyne optics are the same as those shown in FIG. 10, except for a change of physical placement to accommodate different packaging, and will not be discussed further here. A monitoring beam 1131 is reflected from the rear surface of beamsplitter 1111, inclined to the front surface of beamsplitter 1111 by a small angle (typically 1 or 2 degrees), and thereafter diverges from the homodyne beam 1141. The collimated beam 1131 monitors the power and/or the coherence of the light source output. The beam transmitted through the interferometer 1133 impinges upon a detector 1135, which may be a silicon diode sufficiently large to intercept the entire beam and which reports via both DC and AC coupled electronics, the optical power, and any modulation of the sampled light source beam. The thin flat plate interferometer 1133, which may be a small piece of a microscope slide or cover slip, reflects similar intensities from both its not-quite-parallel surfaces. The two similar beams partially overlap sufficiently to produce interference fringes at infinity or elsewhere. Beyond a neutral absorber or rotating polarizer 1137, a monitoring CCTV camera 1139 observes a suitably attenuated image of these fringes, whose high apparent contrast indicates the retention of coherence in the light source. The ideal appearance is of sharply contrasting regions appearing stationary and of constant intensity. Three effects may be usefully monitored by this mechanism. (1) Should the light source mode hop because of an inappropriate combined choice of light source drive current and operating temperature, controlled by the thermoelectric Peltier cooler 1103 and monitored in a closed loop by the thermistor 1105, light source phase jumps will reverse the contrast of the fringes, with the image appearing to skip at right angles to the fringe orientation, or with variable loss of fringe contrast. This condition of unstable light source operation on the boundary between coherent modes may be remedied by slight adjustment, either of light source current or temperature, to place the operating point centrally between adjacent mode transitions. (2) Should the light source receive any coherent feedback from instability within the optical system, the fringes may perhaps shimmer at the mechanical resonant frequency of sources of the parasitic reflection. As is well known in the art, this and any acoustic sensitivity effects must be mitigated by avoidance of significant optical ghosts. (3) Feedback to the light source can arise from particle scattering itself, causing a randomly fluctuating fringe blur and producing parasitic modulation on the homodyne beam. The backscatter frequency modulation of the light source is similar but not identical to the modulation of the scattered beam by direct scattering from the specimen into the receiver. Where the homodyne amplification gain is applied to densely scattering specimens this effect must be allowed for. With certain extreme specimens, such as large, or large numbers of, retro-reflective particles, an error boundary at lower concentration may be introduced that might not otherwise have been suspected, making the independent monitoring in real time a useful feature for certain applications. The parasitic modulation of the light source by backscattered light is of a slightly higher frequency than the desired light at the mean scattering angle by the amount determined by the scattering angle (or conventionally 'q-vector'), and may be compensated during analysis by knowing the relative intensities in the present implementation and under the specific operating conditions during the measurement.

The monitoring portion of the configuration shown in FIG. 11, i.e. beam splitter 1111, interferometer 1131, detector 1135, neutral absorber or rotating polarizer 1137, and CCTV monitoring camera 1139, can also be used in the configurations shown in FIGS. 3 and 8. When adding a beamsplitter to the configurations, such as found in FIGS. 3 and 8, the beamsplitter is positioned in front of the coherent light source to split the illuminating beam. In general, a slightly wedged beamsplitter (depicted in FIGS. 10 and 11) splits an incident beam into three beams comprising a beam reflected from the first face of the beam splitter, a beam reflected from the second face of the beam splitter and refracted twice by the first face, and a twice refracted beam transmitted through the beam splitter. Higher order reflections are either insignificant in power or directed away from later components or both. Either of the two reflected beams may be used for monitoring the illuminating beam intensity and coherence, but it is most convenient and optically optimal to use the refracted reflection from the second surface of the beamsplitter for monitoring, allowing the more aberration free first surface reflection to become the homodyne beam.

The implementations of FIGS. 10 and 11 allow a particularly simple alignment sequence of lockable adjustments and stable retention thereafter. The following sequence uses the labeling of FIG. 11 but applies similarly to FIG. 10, and elsewhere:

(1) Light Source Collimation: Action; translate the lens 1109 with respect to the light source emission surface. Criterion; beam diameter measured by a ruler is the same just after the lens 1109 and several meters beyond.

(2) Receiver Collimation: Action; translate the field stop with respect to the lens 1159 while transilluminating the field stop with another light source of the same wavelength and with the mirror 1155 removed. Criterion; beam diameter measured by a ruler is the same just after the collimating lens 1159 and several meters beyond.

(3) Receiver Focus: Action; replace the mirror 1155 and translate a brushed aluminum plate through the image of the transilluminated field stop. Criterion; scattered speckles appear as large as possible at the best focus where the beam is also smallest and most symmetrical.

(4) Illumination Focus: Action; with the brushed aluminum plate fixed at the best focus of the receiver lens 1127 as above, translate the lens 1115 to adjust axially the light source image to coincide with the best focus of the receiver. Criterion; scattered speckles appear as large as possible at the best focus of the light source, where the beam is also smallest and most symmetrical.

(5) Source Field Overlap: Action; with the brushed aluminum plate fixed, and the transillumination of the field stop removed, steer the angular position of the mirror 1155. Criterion; scattered light is maximally transmitted by the field stop 1163.

(6) Homodyne Focus: Action; axially translate the homodyne focusing lens 1147. Criterion; the homodyne beam uniformly overfills the aperture stop 1157 at its largest opening.

(7) Homodyne Collimation: Action; translate the homodyne collimating lens 1153. Criterion; beam diameter measured by a ruler is constant just after the lens 1153 and several meters beyond. The beamsplitter 1129 need not be removed since it transmits sufficient light to permit the undistorted measurement of collimation.

Note that (6) and (7) may require iteration to meet both criteria simultaneously.

(8) Homodyne Overlap: Action; radially translate (typically using a sprung and lockable grease plate with orthogonal translation screws, or otherwise) the homodyne focusing lens 1147. Criterion; the homodyne beam is maximally transmitted by the field stop 1165, and other reflected ghosts are blocked.

Finally, the detector 1165 is placed sufficiently close to the field stop to assure that all light transmitted by the aperture 1157 and field 1165 stops is detected by the sensitive area of the detector. Less critical placements, for example of the attenuators or the monitoring detector CCD camera, are trivial; but minor adjustments repeating the above sequence may improve signal and homodyne overlap prior to the necessary locking of all adjustments.

FIG. 12 shows an alternative configuration for implementing the homodyne gain, with simpler and fewer critical alignments and greater stability, especially benefiting specimens whose extinction length well exceeds the specimen container breadth, e.g., vial diameter. As with all other implementations described here, the temperature of the coherent light source 1201 is controlled to place the operating point near the middle of the stable region between two adjacent mode transitions by a Peltier cooler 1203, which is monitored in a closed loop by a thermistor 1205. The coherent light source 1201 produces a diverging illuminating cone 1207 that is wholly intercepted by the aperture of a convex aspheric or other lens 1209. FIG. 12 shows a circular vial 1211 containing specimen 1213, but the discussion applies to other specimen geometries where such transmission may be arranged. Light transmitted through the specimen becomes the homodyne beam, unlike the configurations in FIGS. 3, 8, 10, 11, and later 14, where homodyne light bypasses the specimen in an alternative optical path. The transmitted beam is reflected from the front surface of a suitably coated plane mirror 1215, sufficiently thick that the reflection from its rear surface, should that have significant power, is also dumped with the main transmitted beam. A second reflection from the front surface of a suitably coated mirror 1217 further attenuates the beam while returning it to the receiver lens train axis 1239. Three more lenses, a focusing lens 1219, which because of its necessary speed may be aspherical, followed by a collimating lens 1221, and a focusing lens 1223, configure the homodyne beam 1227 to overfill the receiver aperture 1233, assuring a reasonably uniform homodyne spatial intensity distribution. Scattered light enters the diverging visible cone 1225, passes through the lenses 1229 and 1231, the aperture 1233, and the field stop 1235, which is smaller than the homodyne cone 1227 and wholly contained within it. Eventually, both the homodyne beam and the scattered light contained in the diverging receiver cone 1225, overlie each other almost perfectly and reach the surface of the detector 1237 together.

The essence of this alternative homodyne scheme is that the homodyne beam actually passes twice through the specimen. Near forward scattered light from both passes of the transmitted homodyne beam can be proportionally large for predominantly forward scattering particles, typically around 1 micron radius or a bit less. It does not however impair the DLS measurement for two reasons; (1) it is centered on zero frequency, appearing no more than a slight phase change on the unmodulated homodyne beam, and (2) it is also typically already attenuated to about four orders of magnitude below that of the incident beam, from which the required near back scattering arose. However, the homodyne beam intensity is sufficiently larger than the near backscatter so that its amplification is effective and valuable. Since here homodyne is only relevant to transparent specimens that scatter little light, the illuminating beam is transmitted with negligible attenuation.

While it is only necessary that the spatial coherence area for the homodyne beam shall be larger than each van Cittert-Zernike coherence area for the scattered signal beam, here a single speckle of the homodyne beam can readily fill the entire receiving aperture, even when aberrations are present. One desirable consequence of the normally unforgiving Lagrange Invariant is that the homodyne beam is much smaller than the cross section of the illuminated specimen volume at the common point represented by the center of the sensing volume, the center of the vial, and the conjugate image of the field stop. This has some advantage for alignment since the smaller focal diameter may lie anywhere within the conjugate field stop image without detriment. Because the beam is now so highly attenuated, even when more tightly focused, it is sufficiently below any intensity which could affect the specimen, especially in the case here of low absorptivity guaranteed by specimen transparency. All the fixed homodyne advantages described above are thus available in a much simpler apparatus. Furthermore, the added homodyne components, 1215, 1217, 1219, 1221, and 1223, can be integrated as a specialized specimen holder in a Sample Module, allowing possible substitution for other specimen holders such as those discussed previously or others.

FIG. 13 extends the ideas of homodyne amplification of near backscattered light to amplification of light scattered at other angles, of which an arrangement at 90 degrees is shown. This configuration offers the possibility of making measurements of the rotational relaxation rate, from which an estimate of particle aspect ratio may be found. The measured frequency of translational relaxation rate depends upon the sine squared of the scattering angle (the q-vector), whereas the frequency of the rotational diffusion rate is independent of angle. This has permitted good measurements of rotational relaxation rate by measuring the frequency spectrum of the depolarized forward scatter, which is coherently amplified by the unscattered, but typically phase shifted, coherent illuminating beam, using suitable polarization selection, e.g., as described in Digiorgio, et al., Forward depolarized light scattering: heterodyne versus homodyne detection, Physica A, 235, 279, 1997. The former arrangement does not simultaneously, nor easily, measure the translational relaxation rate, from which mean hydrodynamic radius may be found. The extension shown here, typically, but not necessarily, at right angles to the illumination, allows for measurement of both translational and rotational relaxation spectra.

In FIG. 13, fairly polarized (say 100:1) coherent light from the illuminating source 1301 is slightly focused by an aspheric collimator lens 1303 and rendered of much higher polarization purity (say 1e7:1) by a high quality polarizer 1305 aligned so that the 'P' polarization vector is normal to the plane of the diagram. The use of such a polarizer in an only slowly converging beam does not degrade its performance below what is acceptable. The incident beam passes through the specimen 1307 in a specimen container 1309 shown in FIG. 13 as a circular vial, but the discussion suffices for other specimen geometries, as discussed previously. The specimen container whose axis is slightly tilted to prevent optical ghosts from reaching the detector should be free from any significant optical birefringence. The transmitted light becomes a slightly diverging homodyne beam, which is collimated by a lens 1311, redirected by mirrors 1313 and 1319, and increased in diameter by a telescope consisting of short 1315 and longer 1321 focal length lenses, before being redirected by mirror 1327 and refocused by lens 1329 through the center of the earlier illuminated specimen. Beyond the second pass of the specimen, the homodyne beam contained in homodyne cone 1331 continues to diverge until refocused by the receiver achromatic lenses 1333 and 1339, passing through the aperture stop 1337 and a field stop 1341. The divergence of this homodyne beam is sufficient that the illumination over the detector is from a single speckle or van Cittert-Zernike coherence area with a sufficiently uniform intensity to act as an excess local oscillator. The three plane mirrors 1313, 1319, and 1327 are of sufficient thickness to dump second and higher order reflections from the detector field of view, and their surface coatings reflect a suitably attenuated beam without significantly altering the polarization—typically an attenuation factor of 1e4 is sufficient to prevent detector overload (e.g., 1 microwatt for an exemplary avalanche photodiode detector, APD, such as the PerkinElmer C30950E).

Before the second high-quality polarizer 1325, itself necessary to restore the polarization ratio, is a rotatable half-wave plate 1323 to tune the intensity and polarization sufficiently that, when combined with the mirror attenuation, the residual light is of an intensity, diameter and polarization sufficient to act as a homodyne local oscillator to amplify the depolarized light formerly scattered in the direction of the detector 1343 during the first pass, without overloading the detector. This semi-dark field is approached as the polarizer 1325 aligns with the 'S' polarization vector. The third high quality polarizer-analyzer 1335 can be oriented to accept 'P' scattered light from the initial input beam whose frequency is dependent on translational particle motion, or 'S' polarized to accept the amplified depolarized component from the first transit of the cell. In the first case of translationally sensitive 'P' polarized scatter, a shutter 1317 can be closed and the apparatus will operate in the conventional sense to obtain translational information. Alternatively, opening shutter 1317 in 'P' polarization mode allows homodyne gain for translational relaxation measurements, similar to the configuration in FIG. 12. Note that for particles small enough to be in the Rayleigh regime, the 'S' polarized scatter from the 'P' polarized incident beam is vestigially small and can be further extinguished by setting the analyzer 1335 for 'P' transmission.

For Rayleigh particles in the rotationally sensitive case, where the shutter 1317 is closed and the analyzer 1335 is set to accept the depolarized 'S' scattered component, the signal is usually both much smaller and typically of a higher frequency than that of the 'P' scattered beam. Opening of the shutter 1317 allows for homodyne amplification of the 90 degree scattered depolarized component by mixing with the transmitted beam of suitable polarization and coherence. The half-wave plate 1323 and polarizer 1325 accomplish three tasks: 1) they block forward scattered depolarized light emerging after the first pass through the specimen; 2) they rotate the transmitted 'P' polarized beam to 'S' polarized; and 3) they can be used to further adjust the transmitted beam intensity beyond the 1e4 attenuation provided by the mirrors to avoid overloading the detector. Analyzer 1335 rejects the 'P' polarized forward scattered depolarized light after the second pass ('P' polarized because it enters the specimen as 'S' polarized) and allows the 'S' polarized transmitted beam, of suitable polarization and coherence, to mix with and amplify the depolarized light scattered at 90 degrees. As is well known in the art, small adjustments of the rotation of the various polarizing components can adjust relative beam intensities for optimal signal and signal-to-noise ratio. Naturally, all optical components must be as free as possible from parasitic optical birefringence. While this arrangement is easily implemented, the quality of components must be high. An alternative arrangement is shown below in FIG. 14, together with further descriptions which may apply equally to either configuration.

FIG. 14 shows a configuration capable of functionality analogous to that in FIG. 13, but with slightly different properties that may have advantages for alignment, polarization selection, purity of coherence, beam uniformity, and component quality. In FIG. 14 the homodyne does not pass through the vial a second time but bypasses the specimen chamber completely. This markedly reduces the need for optical quality in the specimen container, particularly freedom from birefringence, while retaining some of the alignment tolerance. Indeed, a misplacement even greater than that formerly allowed is now acceptable as long as three conditions are satisfied: (1) the polarization of scattered and homodyne beams is the same; (2) the intensity of the homodyne beam varies little over the aperture; and (3) the typical dimension of each van Cittert-Zernike coherence area in the homodyne beam is larger than speckles from the scattering medium. Slight impairment of the third condition is not catastrophic, but reduces the contrast, i.e. the intercept, of the correlogram In FIG. 14 the coherent light source 1401 produces a beam predominantly 'P' polarized normal to the diagram. A lens 1403 focuses the beam to the center of the specimen 1409, which it reaches after traversing the polarizing beamsplitter 1405 and polarizer 1407. Beamsplitter 1405 reflects most of the 'P' polarized light towards the specimen 1409, from where the light scattered near 90 degrees is collected by the receiving system cone 1411, beyond which it is collimated by the lens 1413 and passed through a polarizer 1415 that may be rotated to transmit either 'P' or 'S' polarized light only. Similar to the configuration in FIG. 10, the homodyne beam emerges 'P' polarized from the beamsplitter 1405, where most of the intensity has been reflected towards the specimen.

The polarization of the homodyne beam is rotated by the half-wave plate 1419 to be either 'P' (half-wave plate axis parallel to incident 'P) or 'S' (half-wave plate axis inclined at 45 degrees to incident 'P), focused by the lens 1421, redirected by the mirror 1425, and recollimated by the lens 1429. Near the focus between lens 1421 and mirror 1425 is a shutter 1423, which may be used to block the homodyne beam when that condition is desired (primarily for translational measurement of specimens that scatter sufficient light). The homodyne beam transmitted by the beamsplitter 1417 is absorbed by a beam dump (not shown). The homodyne beam, whose illumination boundary is defined by homodyne cone 1427, drawn larger than the limits imposed by the lens 1429 in FIG. 14, overfills the aperture 1435 by enough to satisfy a criterion of sufficiently uniform homodyne gain. When the homodyne beam polarization is 'S' oriented, typically used with the polarizer 1415 similarly 'S' oriented, only the depolarized rotational spectrum is amplified sufficiently to be well-measured. Scattered light 1411 is combined in the beamsplitter 1417 with the homodyne light, a coherent sample of the illuminating beam contained within an illuminating cone 1427, passed through the 'S' oriented polarizer 1431 to remove any residual 'P' polarization effects, to converging lens 1433, through aperture 1425 and field 1437 stops to detector 1439.

The configurations in FIGS. 13 and 14 may be operated in any one of four modes, summarized in the table below with approximate performance estimates. In all cases the input polarizer 1407, whose purpose is to improve the light source polarization ratio in the sample illuminating beam, is 'P' oriented. The first two modes are used to measure the translational relaxation rate. In one mode the shutter 1423 is closed (no homodyne amplification), in the other it is open (homodyne amplification). In both modes the half-wave plate 1419, the output polarizer 1415, and the analyzer 1431 are all oriented for 'P' polarization transmission. The third and fourth modes, again with open or closed shutter 1423 (corresponding to no homodyne and homodyne operation, respectively), allow measurement of the rotational relaxation rate, where the half-wave plate 1419, the output polarizer 1415 and the analyzer 1431 are all oriented for 'S' polarization transmission.

For an exemplary estimate of performance, consider a suspension of 10 nm radius particles with a differential refractive index of 1.2, at a volume fractional concentration of 1e-4, exposed to a 658 nm wavelength illumination power of 30 mW. The measurement is made at 90 degrees, where scattering efficiency from spheres is about 1e-3 sr$^{-1}$ for 'P' and about 1e-9 sr$^{-1}$ for 'S' (the Rayleigh 'dip'). With a 50 mm focal length collection lens, the collection solid angle can be as high as 0.0025 sr; where a 100 micron field stop image diameter yields about 200 speckles or coherence areas. The homodyne beam, when present, has a power of about 1 microwatt, sufficient not to overload a typical Avalanche Photodiode Detector, APD such as the PerkinElmer C30950E, whose noise equivalent product (NEP) may be as low as 5e-14 W/√Hz. In an analog detection mode at a gain of 5e5 V/W, the overload condition is typically extended with active DC compensation of the transimpedance amplifier to a few volts. Assuming particles are sufficiently ellipsoidal to give a rotational depolarized scattering efficiency of about 1e-5 sr$^{-1}$, two orders less than translational polarized for 'P' and four orders more than translational polarized for 'S', the DC and AC signal strengths for each of the four operating modes are estimated below. A signal-to-noise ratio of the order of unity or even lower is typically sufficient for reasonable correlation measurements.

| Measurement | Incidence-Detection | Shutter | DC Signal | AC Signal | Signal-to-Noise Ratio |
|---|---|---|---|---|---|
| (1) Translation | 'P-P' | Closed | 1e-8 | 1e-8 | ~200 |
| (2) Amplified Translation | 'P-P' | Open | 1e-6 | 1e-6 | ~40000 |
| (3) Rotation | 'P-S' | Closed | 3e-9 | 3e-9 | ~2 |
| (4) Amplified Rotation | 'P-S' | Open | 1e-6 | 2e-7 | ~400 |

The significance of the above table remains true for a wide range of depolarization scattering efficiencies and mean relaxation rates. It should be noted that in modes (2) and (4) for a large homodyne gain, the measured relaxation times are increased by a factor of two, which may be exploited by reducing the bandwidth accordingly.

Obviously, as the particle concentration, radius and ellipticity reduce, so does the depolarized signal. Smaller sizes also yield higher frequencies and the additional noise further reduces signal-to-noise ratio, so that homodyne gain is proportionally more advantageous for smaller particles, becoming almost essential in the 1 to 10 nm radius range. Homodyne gain is also almost essential for particles differing only slightly from spherical, or of refractive index similar to the suspending fluid.

Almost all of the observations, techniques, caveats, ideas and advantages described in any of the 14 figures should also be considered as applicable to any of the others where that may be possible or could be relevant.

The invention claimed is:

1. An optical system for measuring particle characteristics comprising:
a polarized illuminating beam of light focused in or near a specimen;
polarizing components that selectively pass either 'S' or 'P' polarized homodyne light to mix with at least some of the illuminating beam scattered from the specimen;
polarizing components that selectively pass either 'S' or 'P' polarized scattered light from the specimen; and
a detector receiving both the polarized homodyne beam and polarized scattered light from the specimen,
wherein a conjugate image of a field stop located adjacent the detector is formed at the specimen by a receiving lens and defines a first diameter of a visible volume of the specimen to be substantially equal to a second diameter of the polarized illuminating beam at the specimen.

2. The optical system in claim 1 whereby the homodyne beam phase-front appears to emanate from a region much smaller than the visible volume radius, while being conjugate with a common focal plane of illumination and field stop images.

3. The optical system in claim 1 whereby the optical system comprises a shutter that blocks the homodyne light.

4. The optical system in claim 1 whereby the optical system comprises a polarized homodyne beam transmitted through the specimen.

5. An optical system for measuring particle characteristics comprising:
a polarized illuminating beam of light focused in or near a specimen;
polarizing components that selectively pass either 'S' or 'P' polarized homodyne light to mix with at least some of the illuminating beam scattered from the specimen;
polarizing components that selectively pass either 'S' or 'P' polarized scattered light from the specimen; and
a detector receiving both the polarized homodyne beam and polarized scattered light from the specimen,
whereby the optical system comprises an aperture positioned to receive a visible cone of light from the specimen whereby the aperture allows for more than one coherence area to fall upon a detector, and
wherein a conjugate image of a field stop located adjacent the detector is formed at the specimen by a receiving lens and defines a first diameter of a visible volume of the specimen to be substantially equal to a second diameter of the polarized illuminating beam at the specimen.

6. An optical system for measuring particle characteristics comprising:
a light source;
a sample region configured to hold a droplet on a single transparent plate;
one or more optical components arranged to focus an optical beam from the light source to an illumination volume having a first diameter at a location of the droplet on the transparent plate;
one or more optical components arranged to receive scattered light from a visible volume at the location of the droplet and direct the received scattered light to a detector; and
the detector positioned to receive the scattered light from the location of the droplet, wherein a conjugate image of a field stop located adjacent the detector is formed at the location of the droplet by a receiving lens and defines a first diameter of the visible volume of the droplet to be substantially equal to a second diameter of the illuminating beam at the location of the droplet.

7. An optical system for measuring particle characteristics comprising:
a light source;
a sample region configured to hold a specimen within a translatable wedge shaped container;
one or more optical components arranged to focus an optical beam from the light source to an illumination volume having a first diameter at the sample region;
one or more optical components arranged to receive scattered light from a visible volume at the sample region and direct the received scattered light to a detector; and
the detector positioned to receive the scattered light from the visible volume at the wedge shaped container, wherein a conjugate image of a field stop adjacent the detector is formed at the specimen by a receiving lens and defines a first diameter of a visible volume of the specimen to be substantially equal to a second diameter of the illuminating beam at the specimen.

8. An optical system for measuring particle characteristics by light scattering, the optical system comprising:
a light source;
a sample region configured to hold a sample cell;
a focusing lens arranged to focus an optical beam from the light source to an illumination volume having a first diameter at the sample region;
a receiving lens arranged to receive scattered light from a visible volume at the sample region and direct the received scattered light to a detector; and
an aperture stop having a second diameter and located at the receiving lens, wherein the second diameter admits more than one speckle, as defined by the van Cittert-Zernike coherence theorem, to the detector, wherein a conjugate image of a field stop located adjacent the detector is formed at the specimen by the receiving lens and defines a diameter of the visible volume at the sample region to be substantially equal to the first diameter of the illuminating volume at the sample region.

9. The optical system of claim 8, wherein the second diameter admits up to about 200 speckles to the detector.

10. The optical system of claim 8, wherein the second diameter admits up to about 1000 speckles to the detector.

11. The optical system of claim 8, wherein an intersection of the illumination volume and the visible volume is fully within the sample cell.

12. The optical system of claim 8, wherein the scattered light is received in a rearward direction with respect to an incidence direction of the optical beam on the sample region.

13. The optical system of claim 8, wherein the light source comprises a semiconductor laser.

14. The optical system of claim 8, further comprising:
- a beamsplitter arranged to split the optical beam from the light source and provide a monitoring beam; and
- a detection system configured to receive the monitoring beam and monitor one or both of an intensity and coherence of the optical beam.

* * * * *